US009510946B2

(12) United States Patent
Chau et al.

(10) Patent No.: US 9,510,946 B2
(45) Date of Patent: Dec. 6, 2016

(54) HEART VALVE SEALING DEVICES

(71) Applicant: Edwards Lifesciences Corporation, Irvine, CA (US)

(72) Inventors: Mark Chau, Aliso Viejo, CA (US); Travis Oba, Brea, CA (US); Sergio Delgado, Irvine, CA (US); Robert C. Taft, Irvine, CA (US); Stanton J. Rowe, Newport Coast, CA (US); Alexander H. Cooper, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 98 days.

(21) Appl. No.: 14/011,598

(22) Filed: Aug. 27, 2013

(65) Prior Publication Data

US 2014/0067054 A1    Mar. 6, 2014

Related U.S. Application Data

(60) Provisional application No. 61/697,706, filed on Sep. 6, 2012, provisional application No. 61/763,848, filed on Feb. 12, 2013.

(51) Int. Cl.
*A61F 2/24* (2006.01)

(52) U.S. Cl.
CPC ............ *A61F 2/2436* (2013.01); *A61F 2/243* (2013.01); *A61F 2/246* (2013.01); *A61F 2/2442* (2013.01); *A61F 2/2454* (2013.01); *A61F 2/2463* (2013.01); *A61F 2/2466* (2013.01); *A61F 2/2412* (2013.01); *A61F 2/2433* (2013.01);

(Continued)

(58) Field of Classification Search
CPC .. A61F 2/2442; A61F 2/2445; A61F 2/2448; A61F 2/246; A61F 2/2436; A61F 2/243; A61F 2/2433; A61F 2/24
USPC ........................................................ 623/1.11
See application file for complete search history.

(56) References Cited

U.S. PATENT DOCUMENTS

| 3,409,013 A | 11/1968 | Berry |
| 3,472,230 A | 10/1969 | Fogarty et al. |

(Continued)

FOREIGN PATENT DOCUMENTS

| DE | 2246526 | 3/1973 |
| DE | 19532846 | 3/1997 |

(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

(Continued)

*Primary Examiner* — Christian Sevilla
*Assistant Examiner* — Seema Mathew

(57) ABSTRACT

This disclosure pertains generally to prosthetic devices and related methods for helping to seal native heart valves and prevent or reduce regurgitation therethrough, as well as devices and related methods for implanting such prosthetic devices. In some cases, a spacer having a single anchor can be implanted within a native heart valve. In some cases, a spacer having dual anchors can be implanted within a native heart valve. In some cases, devices can be used to extend the effective length of a native heart valve leaflet.

23 Claims, 26 Drawing Sheets

(52) U.S. Cl.
CPC ........... *A61F 2/2445* (2013.01); *A61F 2/2457* (2013.01); *A61F 2250/0003* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane et al. |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,598 A | 3/1997 | Laufer et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian |
| 6,027,525 A | 2/2000 | Suh et al. |
| 6,042,607 A | 3/2000 | Williamson, IV et al. |
| 6,132,473 A | 10/2000 | Williams et al. |
| 6,165,183 A | 12/2000 | Kuehn et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen |
| 6,245,102 B1 | 6/2001 | Jayaraman |
| 6,269,819 B1 | 8/2001 | Oz et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,447 B1 | 11/2001 | Grimes |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,366 B1 | 10/2002 | Seguin |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,537,290 B2 | 3/2003 | Adams et al. |
| 6,569,196 B1 | 5/2003 | Vesely et al. |
| 6,582,462 B1 | 6/2003 | Andersen et al. |
| 6,605,112 B1 | 8/2003 | Moll |
| 6,626,930 B1 | 9/2003 | Allen et al. |
| 6,629,534 B1 | 10/2003 | St. Goar et al. |
| 6,695,866 B1 | 2/2004 | Kuehn et al. |
| 6,719,767 B1 | 4/2004 | Kimblad |
| 6,730,118 B2 | 5/2004 | Spenser et al. |
| 6,733,525 B2 | 5/2004 | Yang et al. |
| 6,752,813 B2 | 6/2004 | Goldfarb et al. |
| 6,770,083 B2 | 8/2004 | Seguin |
| 6,790,229 B1 | 9/2004 | Berreklouw |
| 6,830,584 B1 | 12/2004 | Seguin |
| 6,875,224 B2 | 4/2005 | Grimes |
| 6,893,460 B2 | 5/2005 | Spenser et al. |
| 6,908,481 B2 | 6/2005 | Cribier |
| 6,974,476 B2 | 12/2005 | McGuckin et al. |
| 7,011,669 B2 | 3/2006 | Kimblad |

(56) References Cited

U.S. PATENT DOCUMENTS

| | | |
|---|---|---|
| 7,018,406 B2 | 3/2006 | Seguin et al. |
| 7,025,791 B2 * | 4/2006 | Levine ............... A61B 17/0401 623/1.11 |
| 7,048,754 B2 | 5/2006 | Martin et al. |
| 7,198,646 B2 | 4/2007 | Figulla et al. |
| 7,201,772 B2 | 4/2007 | Schwammenthal et al. |
| 7,226,467 B2 | 6/2007 | Lucatero et al. |
| 7,276,078 B2 | 10/2007 | Spenser et al. |
| 7,276,084 B2 | 10/2007 | Yang et al. |
| 7,288,097 B2 | 10/2007 | Seguin |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,464,712 B2 | 12/2008 | Oz et al. |
| 7,509,959 B2 | 3/2009 | Oz et al. |
| 7,510,575 B2 | 3/2009 | Spenser et al. |
| 7,524,330 B2 | 4/2009 | Berreklouw |
| 7,530,253 B2 | 5/2009 | Spenser |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,579,381 B2 | 8/2009 | Dove |
| 7,585,321 B2 | 9/2009 | Cribier |
| 7,604,646 B2 | 10/2009 | Goldfarb et al. |
| 7,608,091 B2 | 10/2009 | Goldfarb et al. |
| 7,618,446 B2 | 11/2009 | Andersen et al. |
| 7,621,948 B2 | 11/2009 | Herrmann |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,222 B2 | 4/2010 | Wilk et al. |
| 7,704,269 B2 | 4/2010 | St. Goar et al. |
| 7,736,327 B2 | 6/2010 | Wilk et al. |
| 7,736,388 B2 | 6/2010 | Goldfarb et al. |
| 7,753,923 B2 | 7/2010 | St. Goar et al. |
| 7,758,596 B2 | 7/2010 | Oz et al. |
| 7,803,185 B2 | 9/2010 | Gabbay |
| 7,811,296 B2 | 10/2010 | Goldfarb et al. |
| 7,892,281 B2 | 2/2011 | Seguin et al. |
| 7,914,575 B2 | 3/2011 | Guyenot et al. |
| 7,981,123 B2 | 7/2011 | Seguin |
| 7,993,394 B2 | 8/2011 | Hariton et al. |
| 7,998,151 B2 | 8/2011 | St. Goar et al. |
| 8,007,992 B2 | 8/2011 | Tian et al. |
| 8,029,518 B2 | 10/2011 | Goldfarb et al. |
| 8,029,556 B2 | 10/2011 | Rowe |
| 8,052,592 B2 | 11/2011 | Goldfarb et al. |
| 8,052,750 B2 | 11/2011 | Tuval et al. |
| 8,057,493 B2 | 11/2011 | Goldfarb et al. |
| 8,092,521 B2 | 1/2012 | Figulla et al. |
| 8,118,866 B2 | 2/2012 | Herrmann et al. |
| 8,123,703 B2 | 2/2012 | Martin et al. |
| 8,133,239 B2 | 3/2012 | Oz et al. |
| 8,167,932 B2 | 5/2012 | Bourang |
| 8,187,299 B2 | 5/2012 | Goldfarb et al. |
| 8,206,437 B2 | 6/2012 | Bonhoeffer et al. |
| 8,216,174 B2 | 7/2012 | Wilk et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |
| 8,317,858 B2 | 11/2012 | Straubinger et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,366,767 B2 * | 2/2013 | Zhang ............... A61F 2/2418 623/2.11 |
| 8,398,704 B2 | 3/2013 | Straubinger et al. |
| 8,398,708 B2 * | 3/2013 | Meiri ............... A61B 17/0487 623/2.11 |
| 8,403,983 B2 * | 3/2013 | Quadri ............... A61F 2/2412 623/1.24 |
| 8,407,380 B2 | 3/2013 | Matsunaga |
| 8,409,273 B2 | 4/2013 | Thornton et al. |
| 8,416,643 B2 | 4/2013 | Magee |
| 8,449,599 B2 | 5/2013 | Chau |
| 8,500,761 B2 | 8/2013 | Goldfarb et al. |
| 8,540,767 B2 | 9/2013 | Zhang |
| 8,579,964 B2 * | 11/2013 | Lane ............... A61F 2/2418 623/2.11 |
| 8,579,965 B2 | 11/2013 | Bonhoeffer et al. |
| 8,585,756 B2 | 11/2013 | Bonhoeffer et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,771,347 B2 | 7/2014 | DeBoer et al. |
| 8,778,017 B2 | 7/2014 | Eliasen et al. |
| 8,876,895 B2 | 11/2014 | Tuval et al. |
| 8,926,690 B2 * | 1/2015 | Kovalsky ............... A61F 2/2475 623/1.24 |
| 8,926,691 B2 | 1/2015 | Chau et al. |
| 8,956,404 B2 * | 2/2015 | Bortlein ............... A61F 2/2418 623/2.11 |
| 2001/0005787 A1 | 6/2001 | Oz et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0069593 A1 | 4/2003 | Tremulis et al. |
| 2003/0100939 A1 | 5/2003 | Yodfat et al. |
| 2003/0130731 A1 | 7/2003 | Vidlund et al. |
| 2003/0158597 A1 | 8/2003 | Quiachon |
| 2003/0167071 A1 | 9/2003 | Martin et al. |
| 2003/0212454 A1 | 11/2003 | Scott et al. |
| 2004/0039436 A1 | 2/2004 | Spenser et al. |
| 2004/0049211 A1 | 3/2004 | Tremulis et al. |
| 2004/0092858 A1 | 5/2004 | Wilson et al. |
| 2004/0133263 A1 | 7/2004 | Dusbabek et al. |
| 2004/0167539 A1 | 8/2004 | Kuehn et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173524 A1 * | 8/2006 | Salahieh ............... A61F 2/2439 623/1.11 |
| 2006/0195134 A1 | 8/2006 | Crittenden |
| 2006/0229719 A1 | 10/2006 | Marquez et al. |
| 2006/0241745 A1 * | 10/2006 | Solem ............... A61F 2/2418 623/2.18 |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0027534 A1 | 2/2007 | Bergeim et al. |
| 2007/0038293 A1 | 2/2007 | St.Goar et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |

(56) References Cited

U.S. PATENT DOCUMENTS

| | | |
|---|---|---|
| 2007/0219612 A1* | 9/2007 | Andreas ............ A61B 17/12022 623/1.11 |
| 2007/0270943 A1 | 11/2007 | Solem |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288061 A1 | 11/2008 | Maurer et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1* | 7/2009 | Kveen ................ A61F 2/2418 623/2.11 |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0288634 A1 | 11/2011 | Tuval et al. |
| 2011/0307055 A1 | 12/2011 | Goldfarb et al. |
| 2011/0319989 A1 | 12/2011 | Lane et al. |
| 2012/0022633 A1* | 1/2012 | Olson ................ A61F 2/2418 623/1.11 |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0078350 A1* | 3/2012 | Wang ................ A61F 2/2436 623/2.11 |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0203336 A1* | 8/2012 | Annest ............... A61B 17/0469 623/2.36 |
| 2012/0209374 A1 | 8/2012 | Bonhoeffer et al. |
| 2012/0253386 A1* | 10/2012 | Rowe .................. A61B 17/0293 606/213 |
| 2012/0283823 A1 | 11/2012 | Bonhoeffer et al. |
| 2012/0310336 A1 | 12/2012 | Figulla et al. |
| 2013/0073035 A1 | 3/2013 | Tuval et al. |
| 2013/0079869 A1 | 3/2013 | Straubinger et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0236187 A1 | 8/2014 | Seguin |
| 2014/0236198 A1 | 8/2014 | Goldfarb et al. |
| 2014/0277426 A1* | 9/2014 | Dakin ................ A61F 2/246 623/2.38 |
| 2014/0296878 A1 | 10/2014 | Oz et al. |
| 2016/0015512 A1* | 1/2016 | Zhang ................ A61F 2/2436 623/2.11 |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10010074 | 10/2001 |
| DE | 10049812 | 4/2002 |
| DE | 10049813 | 4/2002 |
| DE | 10049814 | 4/2002 |
| DE | 10049815 | 4/2002 |
| DE | 102006052564 | 12/2007 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1281375 A2 | 2/2003 |
| EP | 1469797 | 10/2004 |
| EP | 1570809 | 9/2005 |
| EP | 1653888 | 5/2006 |
| FR | 2815844 | 5/2002 |
| FR | 2788217 | 7/2007 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | 0060995 A2 | 10/2000 |
| WO | WO 01/28459 | 4/2001 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2005/034812 | 4/2005 |
| WO | WO 2005/087140 | 9/2005 |
| WO | WO 2005/102015 | 11/2005 |
| WO | WO 2006/014233 | 2/2006 |
| WO | WO 2006/034008 | 3/2006 |

(56) References Cited

FOREIGN PATENT DOCUMENTS

| WO | WO 2006/108090 | 10/2006 |
|---|---|---|
| WO | WO 2006/111391 | 10/2006 |
| WO | WO 2006/138173 | 12/2006 |
| WO | WO 2008/005405 | 1/2008 |
| WO | WO 2008/035337 | 3/2008 |
| WO | WO 2008/147964 | 12/2008 |
| WO | WO 2008/150529 | 12/2008 |
| WO | WO 2009/024859 | 2/2009 |
| WO | 2009053952 A2 | 4/2009 |
| WO | WO 2009/116041 | 9/2009 |
| WO | 2011034628 A1 | 3/2011 |
| WO | 2013059747 A1 | 4/2013 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729-34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, $2^{nd}$ Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Médecine et Hygiène, Genève, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Wheatley, M.D., David J., "Valve Prostheses," Rob & Smith's Operative Surgery, Fourth Edition, pp. 415-424, Butterworths 1986.

CN Office Action issued in Application No. 201380057757.8, Issued Dec. 2, 2015.

Supplementary Search Report for European Application No. 13834484, dated Apr. 29, 2016.

* cited by examiner

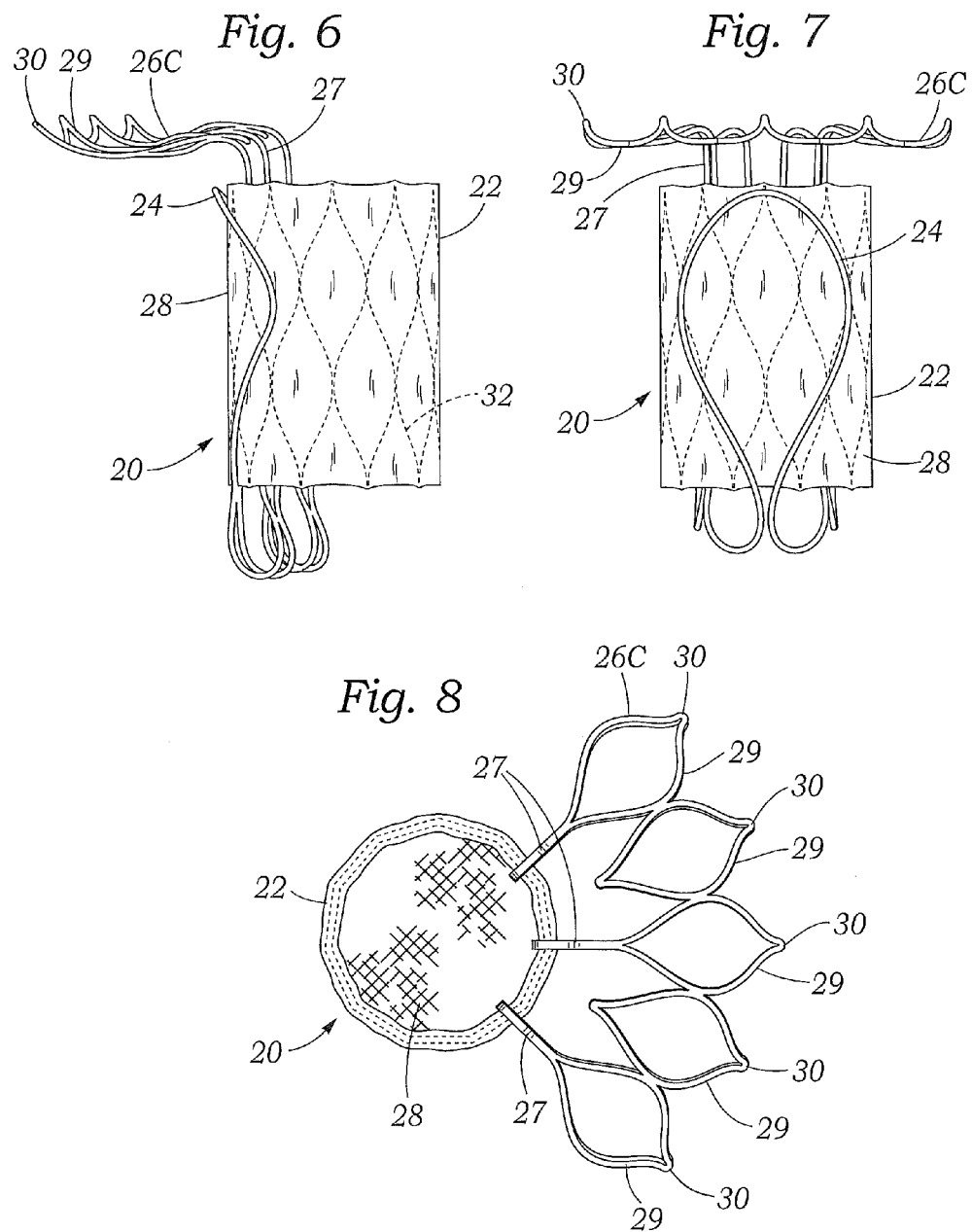

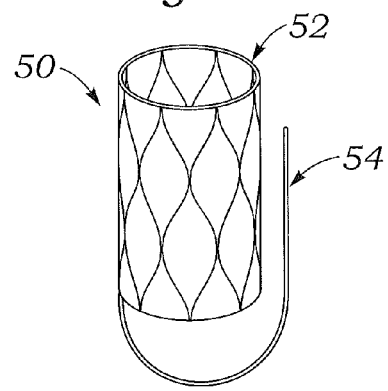
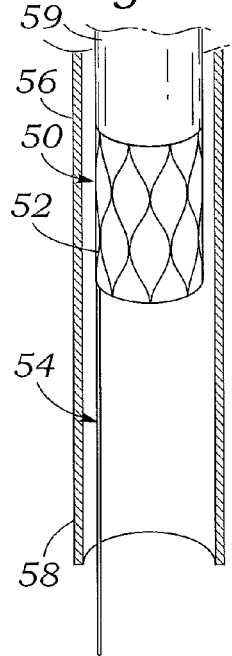
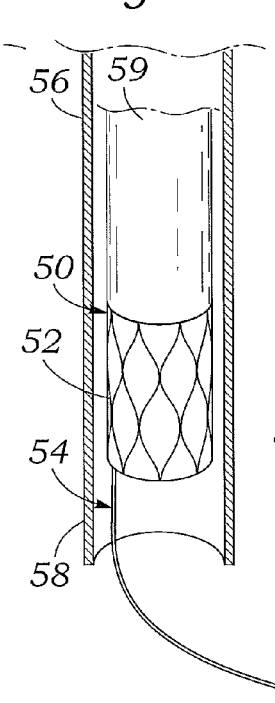
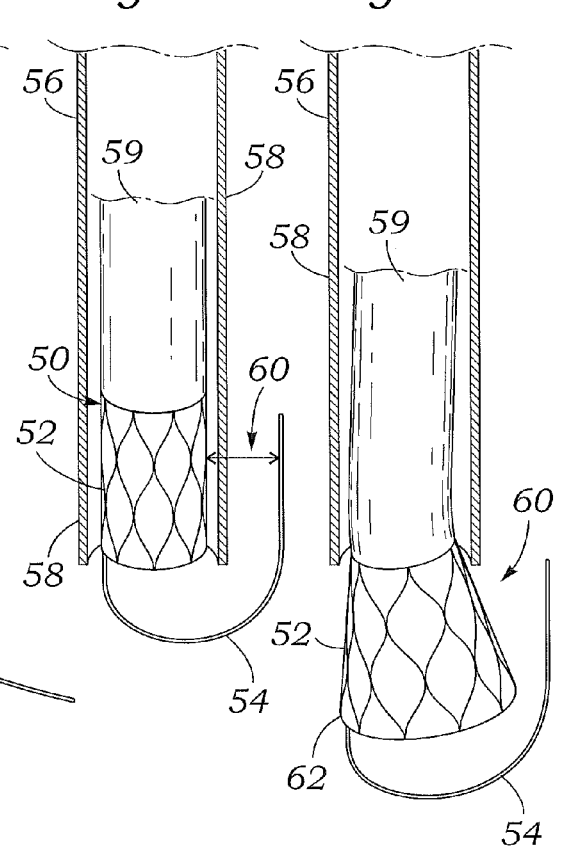

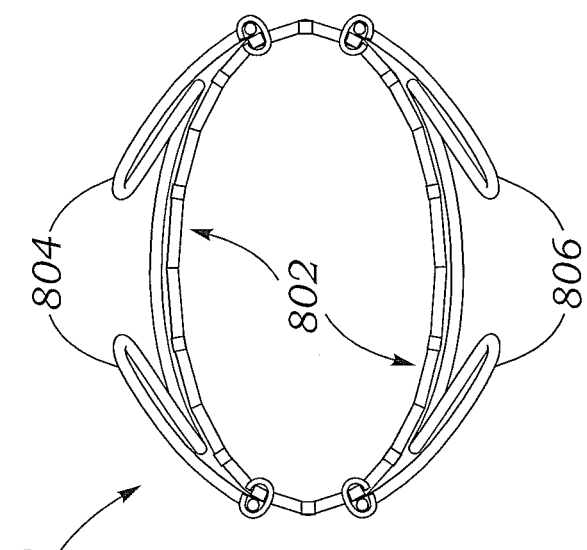
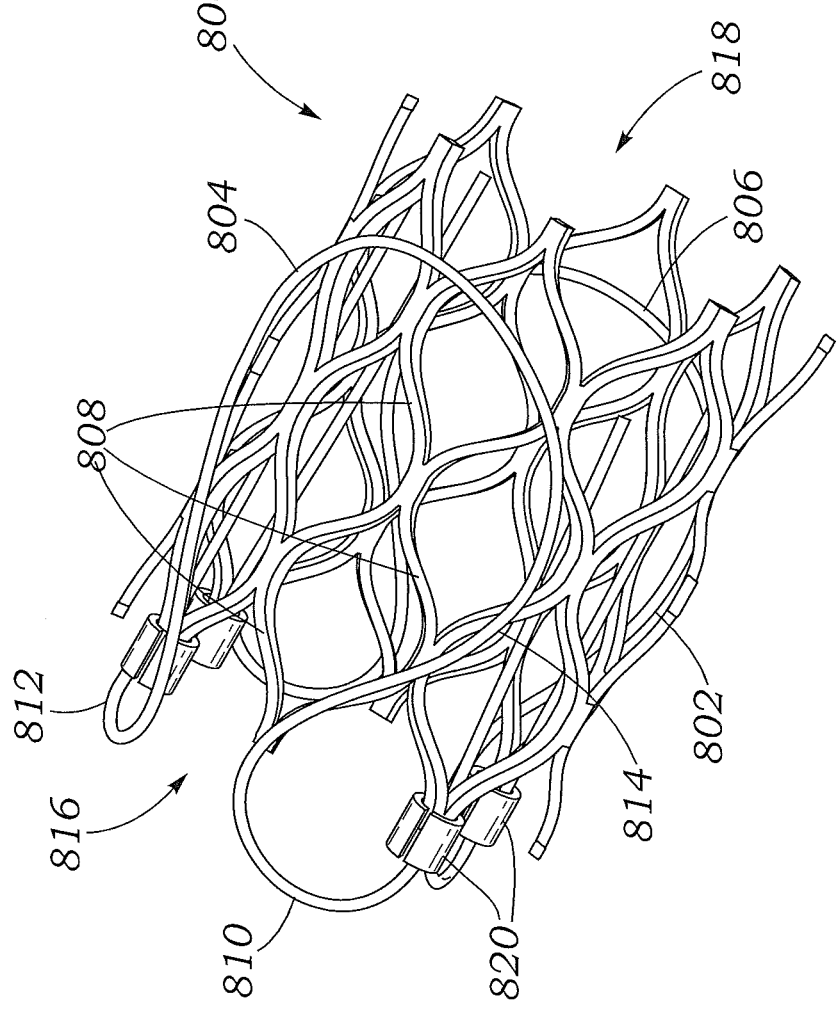

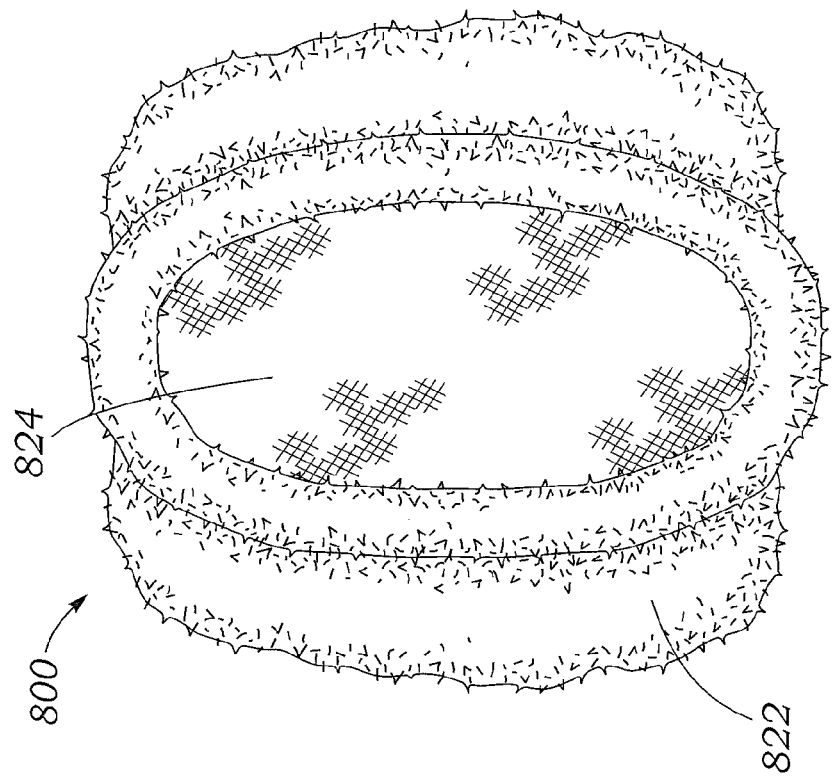
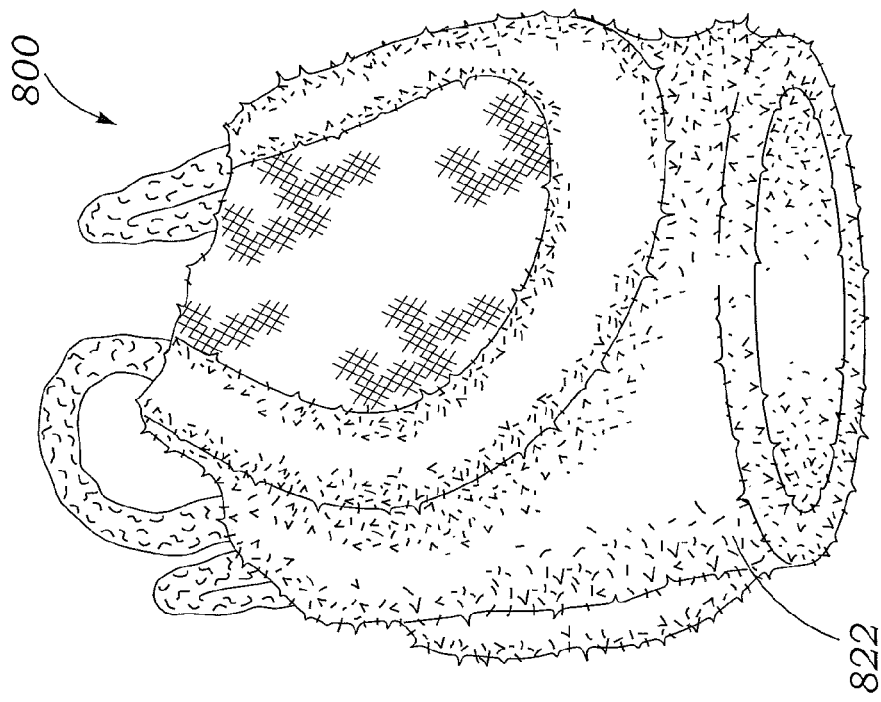

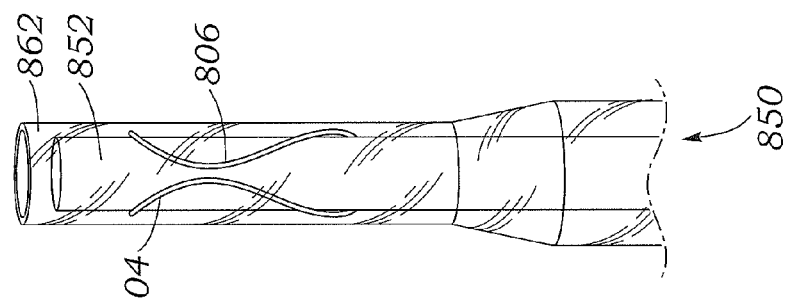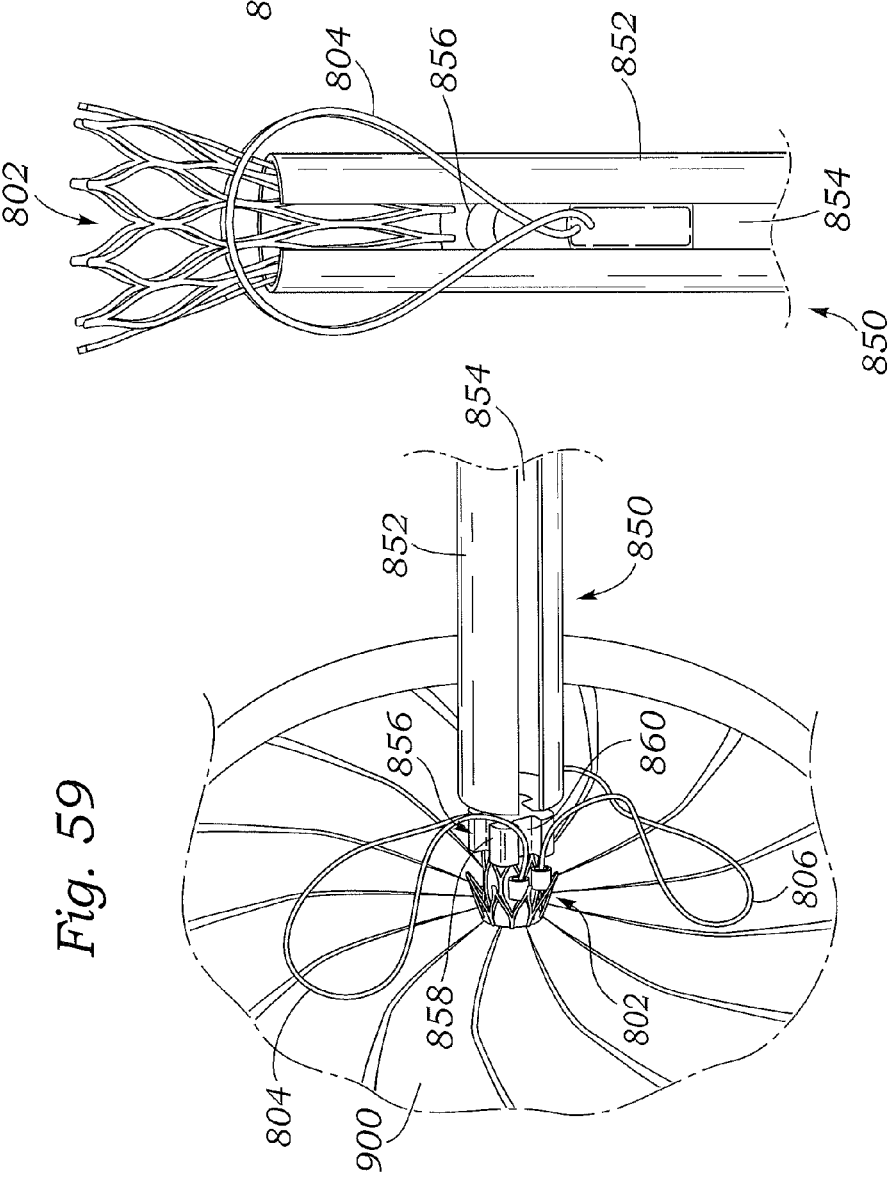

HEART VALVE SEALING DEVICES

CROSS REFERENCE TO RELATED APPLICATIONS

This application claims the benefit of U.S. Provisional Patent Application Nos. 61/697,706, filed Sep. 6, 2012, and 61/763,848, filed Feb. 12, 2013, which are each hereby incorporated herein by reference in their entirety.

FIELD

This disclosure pertains generally to prosthetic devices and related methods for helping to seal native heart valves and prevent or reduce regurgitation therethrough, as well as devices and related methods for implanting such prosthetic devices.

BACKGROUND

The native heart valves (i.e., the aortic, pulmonary, tricuspid and mitral valves) serve critical functions in assuring the forward flow of an adequate supply of blood through the cardiovascular system. These heart valves can be rendered less effective by congenital malformations, inflammatory processes, infectious conditions or disease. Such damage to the valves can result in serious cardiovascular compromise or death. For many years the definitive treatment for such disorders was the surgical repair or replacement of the valve during open heart surgery. However, such surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets extending downward from the annulus into the left ventricle. The mitral valve annulus can form a "D" shaped, oval, or otherwise out-of-round cross-sectional shape having major and minor axes. The anterior leaflet can be larger than the posterior leaflet, forming a generally "C" shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates, the oxygenated blood that is collected in the left atrium flows into the left ventricle. When the muscles of the left atrium relax and the muscles of the left ventricle contract, the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systole phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another. Other prior techniques include the use of a spacer implanted between the native mitral valve leaflets. Despite these prior techniques, there is a continuing need for improved devices and methods for treating mitral valve regurgitation.

SUMMARY

This disclosure pertains generally to prosthetic devices and related methods for helping to seal native heart valves and prevent or reduce regurgitation therethrough, as well as devices and related methods for implanting such prosthetic devices.

In some embodiments, a prosthetic device for treating heart valve regurgitation comprises a radially compressible and radially expandable body having a first end, a second end, and an outer surface extending from the first end to the second end and an anchor having a connection portion and a leaflet capture portion, wherein the connection portion is coupled to the body such that the leaflet capture portion is biased against the outer surface of the body when the body is in a radially expanded state, the prosthetic device is configured to capture a leaflet of a native heart valve between the leaflet capture portion of the anchor and the outer surface of the body, and the body is configured to prevent blood from flowing through the body in a direction extending from the first end to the second end and in a direction extending from the second end to the first end.

In some embodiments, the outer surface of the body comprises a first side against which the anchor is biased and a second side opposite the first side, and the connection portion of the anchor is coupled to the body on the second side of the body. In some embodiments, the anchor comprises an elongated member that is coupled to the second side of the body at a connection location and the elongated member comprises a ventricular portion that extends from the connection location across the first end of the body. In some embodiments, the ventricular portion comprises first and second ventricular portions and the first ventricular portion is substantially parallel to the second ventricular portion.

In some embodiments, the body is radially compressible to a compressed state in which a leaflet-receiving gap exists between the body and the leaflet capture portion of the anchor, and the body is resiliently radially self-expandable to the radially expanded state. In some embodiments, the anchor comprises a first clip portion and a second clip portion, and the device is configured to capture the leaflet between the first and second clip portions. In some embodiments, the body is formed from Nitinol and is radially self-expandable to the expanded state. In some embodiments, the body comprises a metallic frame and a blood-impermeable fabric mounted on the frame. In some embodiments, the body is configured to allow blood to flow around the body between the body and a non-captured leaflet during diastole, and configured to allow the non-captured leaflet to close around the body to prevent mitral regurgitation during systole.

In some embodiments, the anchor is coupled to the first end of the body and the device further comprises an atrial stabilizing member extending from the second end of the body. In some embodiments, the body is configured to move within the native heart valve along with motion of the captured leaflet. In some embodiments, an atrial end portion of the body comprises a tapered shoulder that reduces in diameter moving toward the atrial end portion of the body. In some embodiments, the body comprises a crescent cross-sectional shape. In some embodiments, the anchor comprises first and second anchors and the device is configured to be secured to both native mitral valve leaflets.

In some embodiments, a prosthetic device for treating heart valve regurgitation comprises a main body portion having a connection portion and a free end portion, wherein the connection portion is configured to be coupled to a first one of the two native mitral valve leaflets such that the device is implanted within a native mitral valve orifice, and when the device is implanted within the native mitral valve orifice, the free end portion moves laterally toward a second one of the two native mitral valve leaflets during systole, thereby helping to seal the orifice and reduce mitral regurgitation during systole, and the free end portion moves laterally away from the second native mitral valve leaflet during diastole to allow blood to flow from the left atrium to the left ventricle during diastole.

In some embodiments, the connection portion of the main body is thicker than the free end portion. In some embodiments, the main body portion further comprises an atrial portion that contacts the native mitral valve annulus within the left atrium adjacent to the first native mitral valve leaflet. In some embodiments, the device further comprises a ventricular anchor that clips around a lower end of the first native mitral valve leaflet, thereby securing the device to the first native mitral valve leaflet. In some embodiments, the anchor comprises a paddle shape with a broad upper end portion and a relatively narrow neck portion, wherein the neck portion couples the upper end portion to the main body.

In some embodiments, a prosthetic device comprises a sheet of flexible, blood-impermeable material configured to be implanted within a native mitral valve orifice and coupled to a first one of the two native mitral leaflets or to the native mitral ammlus adjacent the first native mitral leaflet, wherein when implanted the sheet is configured to inflate with blood during systole such that a free portion of the sheet not coupled to the first native mitral leaflet or the mitral annulus adjacent the first native mitral leaflet moves laterally toward and seals against the second of the two native mitral leaflets to reduce mitral regurgitation, and when implanted the sheet is configured to deflate during diastole such that the portion of the sheet not coupled to the first native mitral leaflet or the native mitral annulus adjacent the first native mitral leaflet moves laterally away from the second native mitral leaflet to allow blood to flow from the left atrium to the left ventricle.

In some embodiments, the sheet is supported by a rigid frame that is secured to the first native mitral leaflet. In some embodiments, the frame comprises a ventricular anchor that clips around a lower end of the first native mitral leaflet. In some embodiments, the frame comprises an atrial portion that contacts the native mitral annulus within the left atrium adjacent to the first native mitral leaflet. In some embodiments, an upper end of the sheet is secured directly to the native mitral annulus adjacent the first native mitral leaflet or to the first native mitral leaflet adjacent the native mitral annulus. In some embodiments, the upper end of the sheet is secured to native tissue via rigid anchors that puncture the native tissue.

In some embodiments, the sheet comprises an annular cross-sectional profile perpendicular to an axis extending through the mitral orifice from the left atrium to the left ventricle. In some embodiments, the sheet comprises a closed atrial end and an open ventricular end. In some embodiments, the open lower end is biased toward an open position and is configured to collapse to a closed position during diastole. In some embodiments, the sheet is supported by a rigid frame that is secured to the first native mitral leaflet, and the frame comprises a plurality of longitudinal splines extending from the upper end of the sheet to the lower end of the sheet. In some embodiments, the splines are biased to cause the lower end of the sheet to open away from the first native leaflet.

In some embodiments, a lower end of the sheet is tethered to a location in the left ventricle below the native mitral leaflets. In some embodiments, the lower end of the sheet is tethered to the papillary muscle heads in the left ventricle. In some embodiments, the lower end of the sheet is tethered to a lower end of the rigid frame. In some embodiments, opposing lateral ends of the lower end of the sheet are tethered to the lower end of the frame such that an intermediate portion of the lower end of the sheet can billow out away from the frame and toward the second leaflet during systole. In some embodiments, the sheet has a generally trapezoidal shape, with a broader portion adjacent to the mitral annulus and a narrower portion positioned between the native mitral leaflets.

In some embodiments, a prosthetic device for treating heart valve regurgitation comprises a radially compressible and radially expandable body having a first end, a second end, and an outer surface extending from the first end to the second end, a first anchor coupled to the body and configured to capture the anterior native mitral valve leaflet between the first anchor and the body to secure the device to the anterior leaflet, and a second anchor coupled to the body and configured to capture the posterior native mitral valve leaflet between the second anchor and the body to secure the device to the posterior leaflet, wherein when the first and second anchors capture the anterior and posterior leaflets, the body is situated within a mitral valve orifice between the anterior and posterior leaflets, thereby decreasing a size of the orifice.

In some embodiments, the body is radially compressible to a collapsed delivery configuration suitable for delivering the device to the native mitral valve, and radially expandable from the collapsed delivery configuration to an expanded, operational configuration suitable for operation in the native mitral valve. In some embodiments, the body is formed from Nitinol and is radially self-expandable from the collapsed configuration to the expanded configuration. In some embodiments, the device further comprises a sheet of blood impermeable fabric covering the body. In some embodiments, the body has an elliptical cross-sectional shape. In some embodiments, the body has a crescent cross-sectional shape. In some embodiments, the body comprises a prosthetic valve. In some embodiments, the body is configured to prevent blood from flowing through the body in a direction extending from the first end to the second end and in a direction from the second end to the first end.

In some embodiments, a method of implanting a prosthetic sealing device at a native mitral valve of a heart comprises advancing a delivery catheter to a native mitral valve region of a heart from a left atrium of the heart, the delivery catheter housing the prosthetic sealing device in a radially compressed configuration, advancing the prosthetic sealing device distally relative to the delivery catheter such that an anchor of the prosthetic sealing device moves out of the catheter and forms a leaflet-receiving gap between an end portion of the anchor and the delivery catheter, positioning either a posterior or an anterior mitral valve leaflet in the gap, and advancing a radially compressed body of the prosthetic sealing device out of the delivery catheter such that the body self-expands radially toward the end portion of the anchor, reducing the gap, and capturing the leaflet between the body and the end portion of the anchor, wherein the body is configured to prevent the flow of blood through the body during systole and during diastole.

In some embodiments, a non-captured one of the anterior and posterior leaflets is not secured to the prosthetic sealing device when the prosthetic sealing device is implanted at the native mitral valve. In some embodiments, advancing a delivery catheter through the native mitral valve from a left atrium comprises advancing the delivery catheter through an incision in a portion of a septum between the left atrium and a right atrium. In some embodiments, when the delivery catheter is advanced to the native mitral valve region of the heart, the anchor is held in a substantially straightened position within the delivery catheter extending distally from body of the prosthetic sealing device.

In some embodiments, a method of implanting a prosthetic sealing device at a native mitral valve comprises advancing a delivery device to a native mitral valve region via a left ventricle, the delivery catheter housing the prosthetic sealing device in a compressed configuration, allowing an anchor of the prosthetic sealing device to move radially out of the delivery device while a body of the delivery device is in a compressed configuration, such that a leaflet-receiving gap forms between an end portion of the anchor and the delivery device, positioning either a posterior or an anterior mitral valve leaflet in the gap, and allowing the body of the prosthetic sealing device to radially self-expand such that the leaflet is captured between the body and the anchor, wherein the body is configured to prevent the flow of blood through the body during systole and during diastole.

In some embodiments, a non-captured one of the anterior and posterior mitral valve leaflets is not secured to the prosthetic sealing device when the prosthetic sealing device is implanted at the native mitral valve. In some embodiments, advancing a delivery device to a native mitral valve region via a left ventricle comprises inserting the delivery device into the left ventricle through an incision in an apex of the left ventricle.

In some embodiments, a method of implanting a prosthetic sealing device at a native mitral valve of a heart comprises advancing a delivery system to a native mitral valve region of a heart from a left ventricle of the heart, the delivery system housing the prosthetic sealing device in a radially compressed configuration, proximally retracting an outer sheath of the delivery system such that anchors of the prosthetic sealing device are not confined within the delivery system, advancing the delivery system toward the left atrium of the heart such that native mitral valve leaflets are positioned between the anchors of the prosthetic sealing device and the delivery system, proximally retracting an inner sheath of the delivery system such that a body of the prosthetic sealing device is not confined within the delivery system, wherein the body is configured to prevent the flow of blood through the body during systole and during diastole, and removing the delivery system from the native mitral valve region of the heart.

In some embodiments, advancing the delivery system to the native mitral valve region from the left ventricle comprises inserting the delivery device into the left ventricle through an incision in an apex of the left ventricle. In some embodiments, when the delivery system is advanced to the native mitral valve region of the heart, the anchor is held in a substantially straightened position within the delivery catheter extending distally along a side of the body of the prosthetic sealing device.

In some embodiments, a method of implanting a prosthetic sealing device at a native mitral valve of a heart comprises advancing a delivery system to a native mitral valve region of a heart from a left atrium of the heart, the delivery system housing the prosthetic sealing device in a radially compressed configuration, proximally retracting an outer sheath of the delivery system such that anchors of the prosthetic sealing device are not confined within the delivery system, retracting the delivery system toward the left atrium of the heart such that native mitral valve leaflets are positioned between the anchors of the prosthetic sealing device and the delivery system, proximally retracting an inner sheath of the delivery system such that a body of the prosthetic sealing device is not confined within the delivery system, wherein the body is configured to prevent the flow of blood through the body during systole and during diastole, and removing the delivery system from the native mitral valve region of the heart.

In some embodiments, advancing the delivery system to the native mitral valve region from the left atrium comprises advancing the delivery system through an incision in a portion of a septum between the left atrium and a right atrium. In some embodiments, when the delivery system is advanced to the native mitral valve region of the heart, the anchor is held in a substantially straightened position within the delivery catheter extending proximally from body of the prosthetic sealing device.

BRIEF DESCRIPTION OF THE DRAWINGS

FIG. 6 is a side view of an exemplary sealing device.

FIG. 7 is another side view of the sealing device of FIG. 6.

FIG. 8 is an atrial end view of the sealing device of FIG. 6.

FIG. 11 shows a sealing device having an anchor that extends from one side of a body, around a ventricular end of the body, and along a second side of the body.

FIGS. 12-15 show a method of deploying the sealing device of FIG. 11 from a delivery sheath.

FIGS. 55 and 56 show another exemplary prosthetic device comprising a radially compressible and expandable body.

FIGS. 57 and 58 show the prosthetic device of FIGS. 55 and 56 with a fabric layer.

FIGS. 59-63 show an exemplary prosthetic device with an exemplary delivery system, in various configurations.

DETAILED DESCRIPTION

Figure 1:
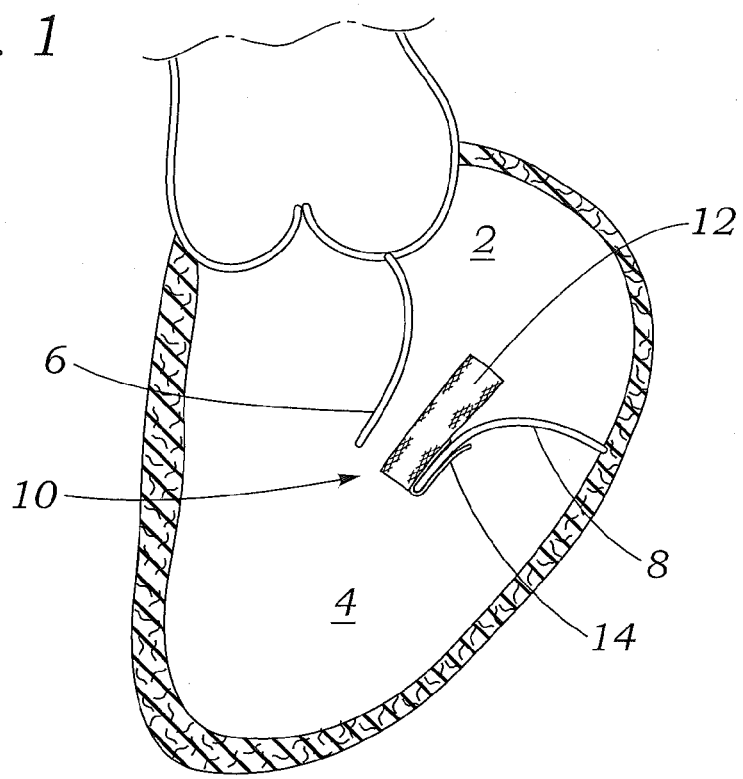
FIG. 1 shows a portion of a human heart with an exemplary embodiment of a sealing device attached to the native posterior mitral leaflet.

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native mitral valve. The disclosed embodiments should not be construed as limiting in any way. Instead, the present disclosure is directed toward all novel and nonobvious features and aspects of the various disclosed embodiments, alone and in various combinations and sub-combinations with one another.

Prosthetic Spacers

In some embodiments, a prosthetic device comprises a body and an anchor. The body is configured to be positioned within the native mitral valve orifice to help create a more effective seal between the native leaflets to prevent or minimize mitral regurgitation. The body can comprise a structure that is impervious to blood and that allows the native leaflets to close around the sides of the body during ventricular systole to block blood from flowing from the left ventricle back into the left atrium. The body is sometimes referred to herein as a spacer because the body can fill a space between improperly functioning native mitral leaflets that do not naturally close completely. In some embodiments, the body can comprise a prosthetic valve structure positioned within an annular body.

The body can have various shapes. In some embodiments, the body can have an elongated cylindrical shape having a round cross-sectional shape. In other embodiments, the body can have an ovular cross-sectional shape, a crescent cross-sectional shape, or various other non-cylindrical shapes. The body can have an atrial or upper end positioned in or adjacent to the left atrium, a ventricular or lower end positioned in or adjacent to the left ventricle, and an annular side surface that extends between the native mitral leaflets.

The anchor can be configured to secure the device to one or both of the native mitral leaflets such that the body is positioned between the two native leaflets. The anchor can attach to the body at a location adjacent the ventricular end of the body. The anchor can be configured to be positioned behind a native leaflet when implanted such that the leaflet is captured between the anchor and the body.

The prosthetic device can be configured to be implanted via a delivery sheath. The body and the anchor can be compressible to a radially compressed state and can be self-expandable to a radially expanded state when compressive pressure is released. The device can be configured to allow the anchor to self-expand radially away from the still-compressed body initially in order to create a gap between the body and the anchor. The leaflet can then be positioned in the gap. The body can then be allowed to self-expand radially, closing the gap between the body and the anchor and capturing the leaflet between the body and the anchor. The implantation methods for various embodiments can be different, and are more fully discussed below with respect to each embodiment. Additional information regarding these and other delivery methods can be found in U.S. Patent Application Publication No. 2011/0137397 and U.S. Provisional Patent Application No. 61/760,577, which are incorporated by reference herein in their entirety.

Some embodiments disclosed herein are generally configured to be secured to only one of the native mitral leaflets. However, other embodiments comprise more than one anchor and can be configured to be secured to both mitral leaflets. Unless otherwise stated, any of the embodiments disclosed herein that comprise a single anchor can optionally be secured to the anterior mitral leaflet or secured to the posterior mitral leaflet, regardless of whether the particular embodiments are shown as being secured to a particular one of the leaflets.

Furthermore, some embodiments can optionally also include one or more atrial anchors, such as to provide additional stabilization. Unless otherwise stated, any of the embodiments disclosed herein can optionally include an atrial anchor or not include an atrial anchor, regardless of whether the particular embodiments are shown with an atrial anchor or not.

Some of the disclosed prosthetic devices are prevented from atrial embolization by having the anchor hooked around a leaflet, utilizing the tension from native chordae tendinae to resist high systolic pressure urging the device toward the left atrium. During diastole, the devices can rely on the compressive forces exerted on the leaflet that is captured between the body and the anchor to resist embolization into the left ventricle.

Figure 2:
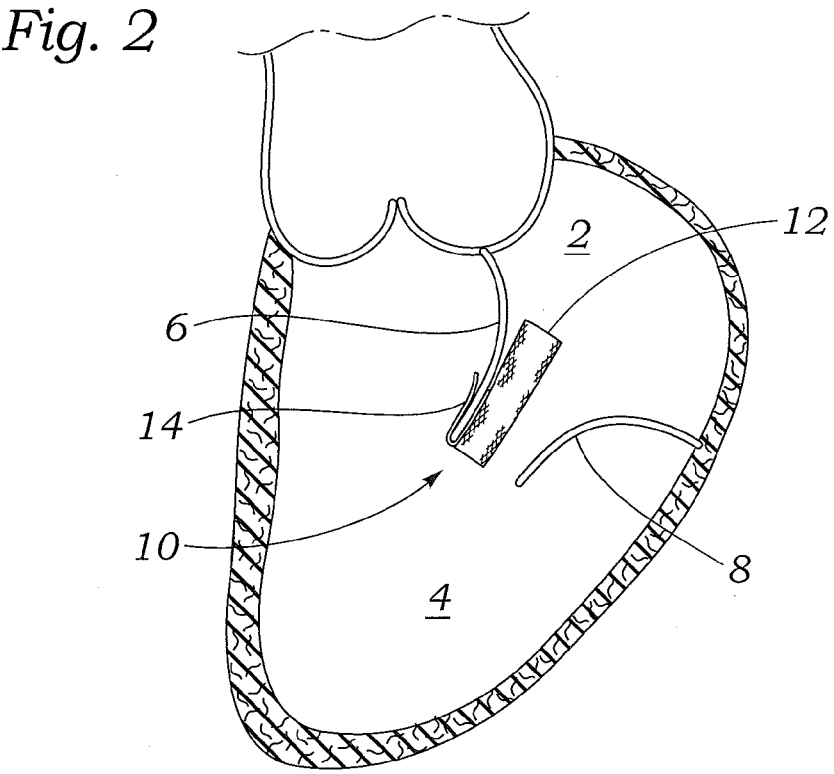
FIG. 2 shows a portion of a human heart with an exemplary embodiment of a sealing device attached to the native anterior mitral leaflet.

FIG. 1 shows an exemplary embodiment of a prosthetic device 10 that comprises a body 12 and an anchor 14. The device 10 is secured to the posterior mitral leaflet 8 with the free end of the leaflet 8 captured between the anchor 14 and the body 12. In FIG. 1, the anterior mitral leaflet 6 is shown separated from the body 12 during diastole as blood flows from the left atrium 2 into the left ventricle 4. As the mitral leaflets open apart from each other, the device 10 can move with the posterior leaflet 8, allowing the anterior leaflet 6 to open away from the body 12. During systole, the back pressure on the leaflets closes them together around the body 12 to prevent mitral regurgitation. FIG. 2 shows the device 10 alternatively secured to the anterior mitral leaflet 6 with the posterior mitral leaflet 8 free to articulate toward and away from the device 10.

Figure 3:
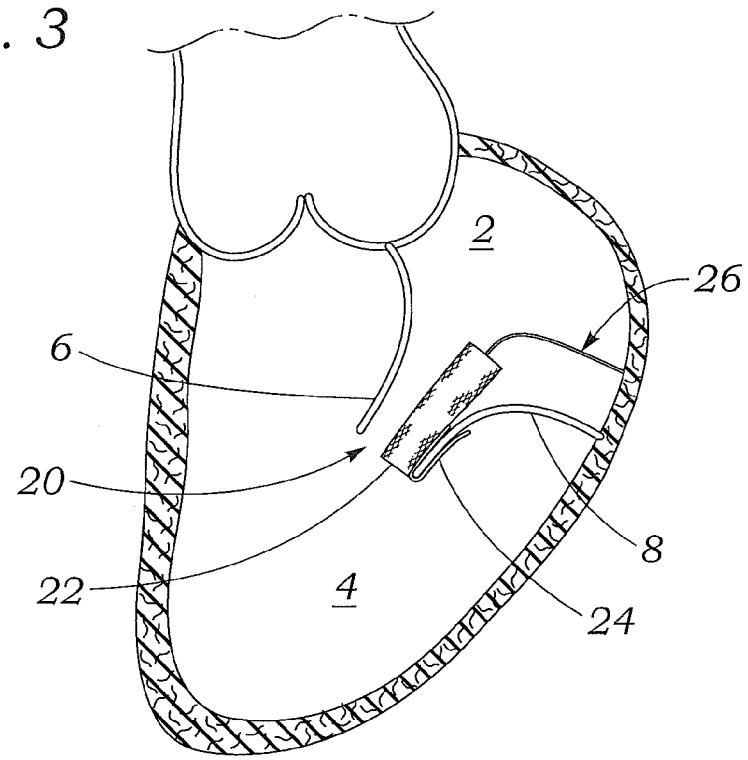
FIG. 3 shows a portion of a human heart with an exemplary embodiment of a sealing device attached to the native posterior mitral leaflet and having an atrial anchor.

FIG. 3 shows a prosthetic device 20 having a body 22, a ventricular anchor 24, and an atrial anchor 26. The device 20 is shown secured to the posterior leaflet 8 via the ventricular anchor 24. The atrial anchor 26 can extend laterally from adjacent the atrial end of the body 22 toward the mitral annulus or other lateral portions of the left atrium 2 adjacent to the posterior leaflet 8. The atrial anchor 26 can help stabilize the device. For example, the atrial anchor 26 can prevent the body 22 from tilting and keep it oriented longitudinally along the blood flow direction through the mitral orifice. The atrial anchor 26 can also help prevent the device 20 from embolizing into the left ventricle 4.

Figure 4:
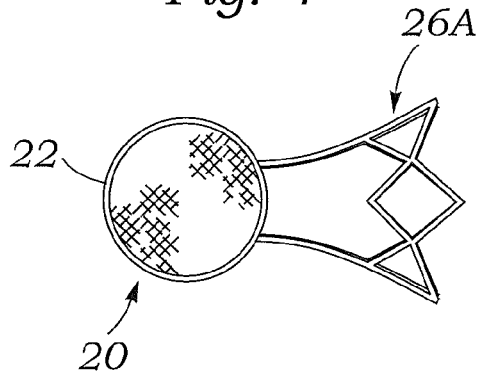
FIG. 4 is an atrial end view of one embodiment of the sealing device of FIG. 3 having a lattice-type atrial anchor.
Figure 5:
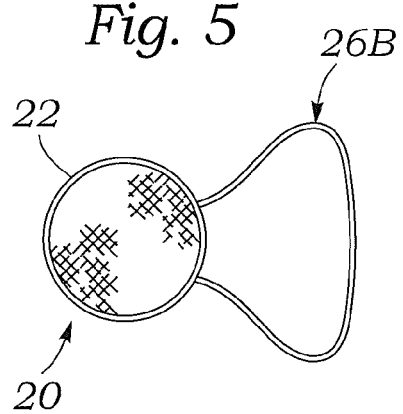
FIG. 5 is an atrial end view of another embodiment of the sealing device of FIG. 3 having a loop-type atrial anchor.

FIGS. 4 and 5 are atrial end views showing two alternative embodiments of atrial anchors for the device 20. FIG. 4 shows an atrial anchor 26A that comprises a lattice-type framework supported by two connections to the body 22, while FIG. 5 shows an atrial anchor 26B that comprises a single elongated member extending in a loop between two connections to the body 22. In both embodiments, the atrial anchor comprises a relatively broader or wider end portion configured to engage with the atrial tissue so as to spread out the engagement forces to avoid tissue damage and promote increased tissue ingrowth.

FIGS. 6-8 show three views of an exemplary embodiment of the prosthetic device 20 having a cylindrical body 22, a ventricular anchor 24, and an atrial anchor 26C. The ventricular anchor 24, as shown in FIGS. 6 and 7, comprises an elongated member that extends from two connection points adjacent the ventricular end of the body 22 and along one side of the body toward the atrial end of the body. The ventricular anchor is contoured around the generally cylindrical side surface of the body 22. The atrial anchor 26C comprises a lattice-type framework made up of several diamond-shaped segments 29 coupled side-by-side in an arc. The atrial anchor 26C further comprises three connecting members 27 coupling it to the body 22 adjacent the atrial end of the body. As shown in FIG. 6, the atrial member 26C extends generally laterally to the same side of the body 22 as the ventricular anchor 24. The radially outward end portion of the atrial anchor can have an upward curvature to conform to the curved geometry of the left atrium. Each of the diamond-shaped segments 29 comprises radially outwardly pointing tip 30 that can press into and/or penetrate adjacent tissue in some cases.

The device 20 is shown in an expanded configuration in FIGS. 3-9. In a compressed delivery configuration, the atrial anchor 26 can be folded down against the side of the body 22 or extended upwardly away from the body 22. Furthermore, the atrial anchor 26 can be circumferentially compressed, especially embodiments having a lattice-type structure.

The body 22 can comprise an annular metal frame 32 covered with a blood-impervious fabric 28, as shown in FIGS. 6-9. One or both ends of the body can also be covered with the blood-impervious fabric 28, as shown in FIG. 8. The frame 32 can comprise a mesh-like structure comprising a plurality of interconnected metal struts, like a conventional radially compressible and expandable stent. In other embodiments, the body can comprise a solid block of material, such as flexible sponge-like block. In some embodiments, the body 22 can be hollow or filled with material.

The frame 32 can be formed from a self-expandable material, such as Nitinol. When formed from a self-expandable material, the frame 32 can be radially compressed to a delivery configuration and can be retained in the delivery configuration by placing the device in the sheath of a delivery apparatus. When deployed from the sheath, the frame 32 can self-expand to its functional size. In other embodiments, the frame can be formed from a plastically expandable material, such as stainless steel or a cobalt chromium alloy. When formed from a plastically expandable material, the prosthetic device can be crimped onto a delivery apparatus and radially expanded to its functional size by an inflatable balloon or an equivalent expansion mechanism. It should be noted that any of the embodiments disclosed herein can comprise a self-expandable main body or a plastically expandable main body.

Figure 9:
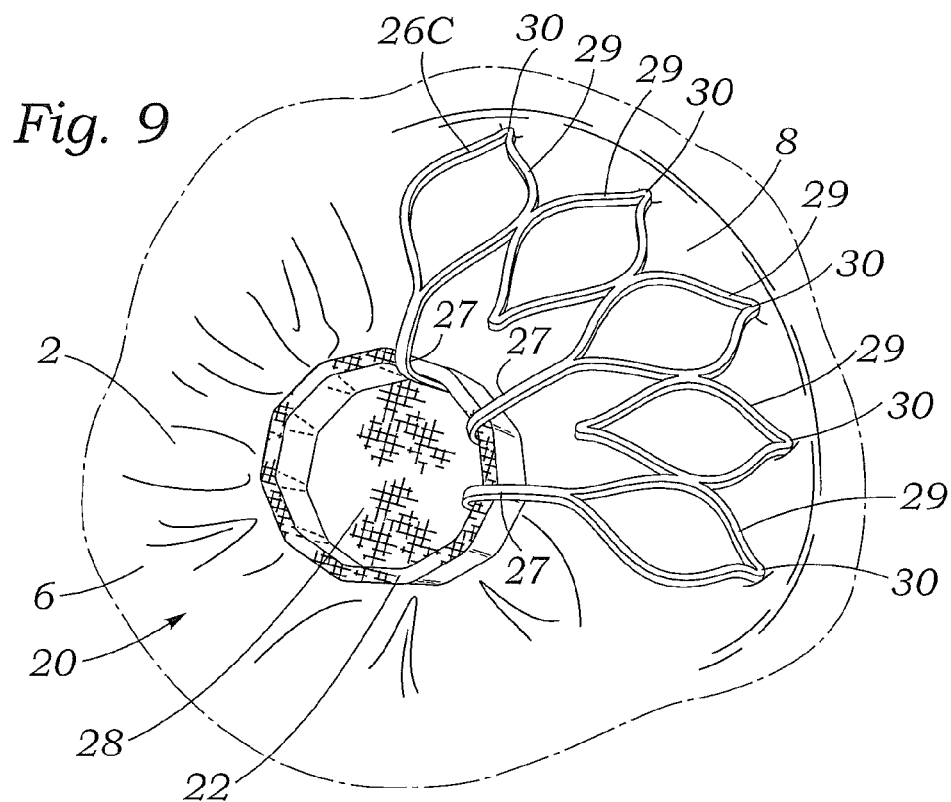
FIG. 9 is an atrial end view of the sealing device of FIG. 6 implanted at a native mitral valve.

FIG. 9 is a view from the left atrium 2 of the device 20 of FIGS. 6-8 implanted at a mitral valve. The body 22 is positioned between the native leaflets 6, 8 in a sealed position with the atrial anchor 26C engaged with the atrial tissue adjacent the posterior mitral leaflet 8. The atrial end of the body 22 is open while the ventricular end of the body is covered with the impervious fabric 28.

Figure 10:
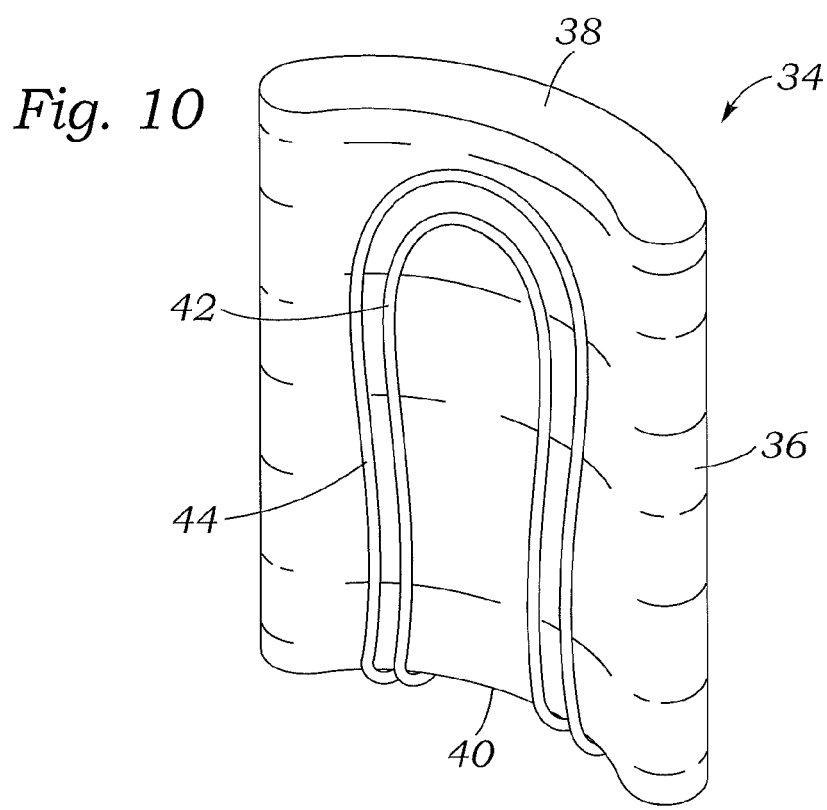
FIG. 10 shows a crescent-shaped embodiment of a sealing device.

FIG. 10 shows an exemplary prosthetic device 34 having a crescent shaped body 36. The body 36 is configured to be positioned with the convex side facing the posterior mitral leaflet 8 and the concave side facing the anterior mitral leaflet 6. In this embodiment, the body 36 can comprise a flexible, sponge-like material. Consequently, the device 34 can comprise two ventricular anchors to capture the anterior leaflet 6. A first ventricular anchor 44 is configured to be positioned behind the anterior leaflet while a second ventricular anchor 42 is configured to be positioned between the body 36 and the anterior leaflet. The anterior leaflet 6 is therefore captured and pinched between the two anchors 42, 44 to secure the body 36 within the mitral orifice. The device 34 relies on the two anchors 42, 44 to capture the leaflet because the body 36 in this embodiment may lack sufficient rigidity to grip the leaflet. Both of the ventricular anchors 42, 44 can extend from adjacent a ventricular end 40 of the body 36 and extend up toward an atrial end 38 of the body along the same side of the body. In other embodiments, the anchors 42, 44 can be positioned on the convex side of the body 36 in order to secure the body to the posterior leaflet. In some embodiments, the anchor 42 can be nested within the anchor 44 to provide a smaller crimped profile. In other embodiments, the anchors 42, 44 can have various other shapes. In still other embodiments, the body 36 can be cylindrical or can have any of various other shapes described herein.

FIG. 11 shows an exemplary embodiment of a prosthetic device 50 having a body 52 and an anchor 54 that attaches to a first side of the body, extends around the ventricular end of the body, and extends along a second side of the body opposite the first side of the body. The device 50 is configured to capture a mitral leaflet between the anchor 54 and the second side of the body 52 to secure the body within the mitral orifice. The body 52 can comprise, for example, a radially compressible and expandable metal stent covered by a blood impermeable fabric, as described above.

FIGS. 12-15 illustrate an exemplary method of deployment of the device 50 from a delivery catheter 56. In FIG. 12, the body 52 is shown in a radially compressed state within the catheter 56 with the anchor 54 extending distally from the ventricular end of the body in a straightened, or unfurled, state. The device 50 can be resiliently deformed in this configuration such that the device 50 resiliently returns to the configuration shown in FIG. 11 when released from constraint. A pusher member 59 can be used to push the device 50 distally relative to the catheter 56 or to hold the device 50 steady as the catheter is retracted. In FIG. 13, the catheter 56 is retracted proximally from the device 50 and/or the device 50 is advanced distally from the catheter 56 such that the elongated anchor 54 begins to extend out of the distal outlet 58 of the catheter. As the anchor 54 moves out of the outlet 58, the anchor begins to naturally return toward the shape of FIG. 11, curling gradually as it is freed from the confining forces of the catheter. In FIG. 14, the entire anchor 54 has moved out of the catheter 56 and has returned to its natural shape of FIG. 11. However, the body 52 is still held in radial compression by the catheter, creating a gap 60 between the second side of the body 52 and the end of the anchor 54. A mitral leaflet can be positioned within the gap 60 while the device is in the configuration of FIG. 14. In FIG. 15, the ventricular end 62 of the body 52 begins to advance out of the outlet 58, allowing the ventricular end 62 of the body to radially expand while the atrial end 64 of the body remains held in compression within the catheter. This causes the body 52 to expand gradually toward the anchor 54, decreasing the width of the gap 60, thereby capturing the leaflet within the gap. Once the atrial end 64 of the body 52 is freed from the catheter 56, the entire body 52 can expand to its fully expanded state shown in FIG. 11, pinching or compressing the leaflet between the end of the anchor 54 and the side of the body. In the fully expanded state shown in FIG. 11, a gap remains between the body 52 and the anchor 54, although the gap is desirably sized such that a leaflet is engaged by the body and the anchor when placed in the gap. In alternative embodiments, however, such a gap may not exist when the device is in its fully expanded state (i.e., the anchor 54 contacts the body 52 when a leaflet is not positioned between these two components).

Figure 16:
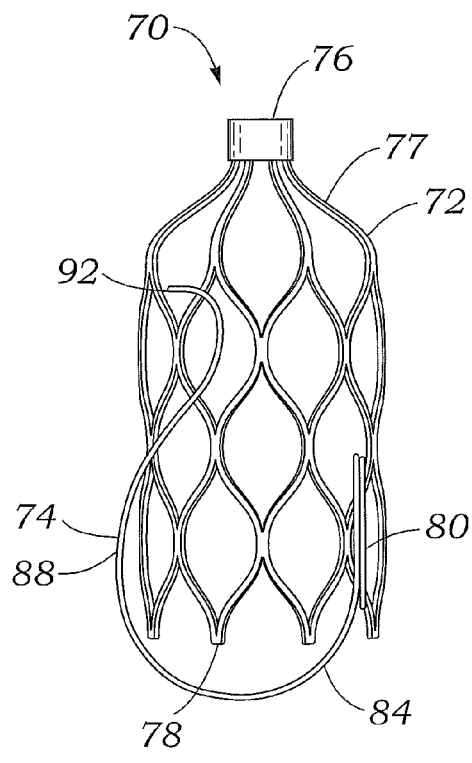
FIG. 16 is a side view of another embodiment of a sealing device having an anchor that extends from one side of a body, around a ventricular end of the body, and along a second side of the body.
Figure 17:
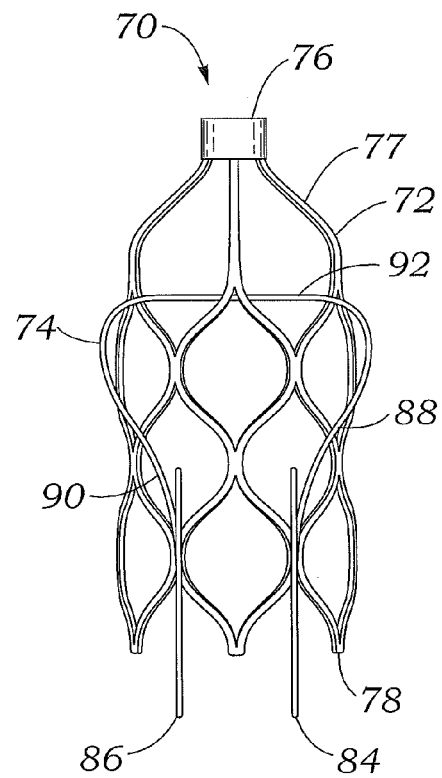
FIG. 17 is another side view of the embodiment of FIG. 16.
Figure 18:
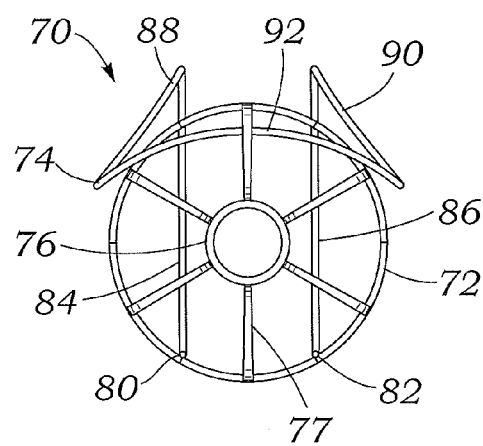
FIG. 18 is an atrial end view of the embodiment of FIG. 16.

FIGS. 16-18 show orthogonal views of an exemplary embodiment of a device 70 similar to the device 50. The device 70 can be deployed from a catheter in the manner described above with respect to FIGS. 11-15. The device 70 comprises a radially self-expandable body 72 and a ventricular anchor 74. The body 72 can comprise a narrowed atrial end 76 and a tapered shoulder region 77, such as to provide improved hemodynamics as blood flows around the shoulder region. The body 72 has a ventricular end 78 opposite from the atrial end 76. The ventricular anchor 74 can comprise an elongated, curved member that connects to the body 72 at two connection points 80, 82 adjacent to the ventricular end 78 on a first side of the body (i.e., the right side of the body in FIG. 16). As shown in FIGS. 16-18, the anchor 74 comprises first portions 84, 86 that extend from the connection points 80, 82, respectively, around the ventricular end 78 of the body, to a second, opposite side of the body (i.e., the left side of the body in FIG. 16). The anchor 74 further comprises second portions 88, 90 that extend from the first portions 84, 86, respectively, along the second side of the body toward the atrial end 76 of the body. The second portions 88, 90 gradually expand apart from each other moving atrially toward an end portion 92 of the anchor 74. The second portions 88, 90 and the end portion 92 of the anchor 74 can form a paddle shape, as shown in FIG. 17, and can have a circumferential curvature that substantially matches the curvature of the body 72.

Figure 19:
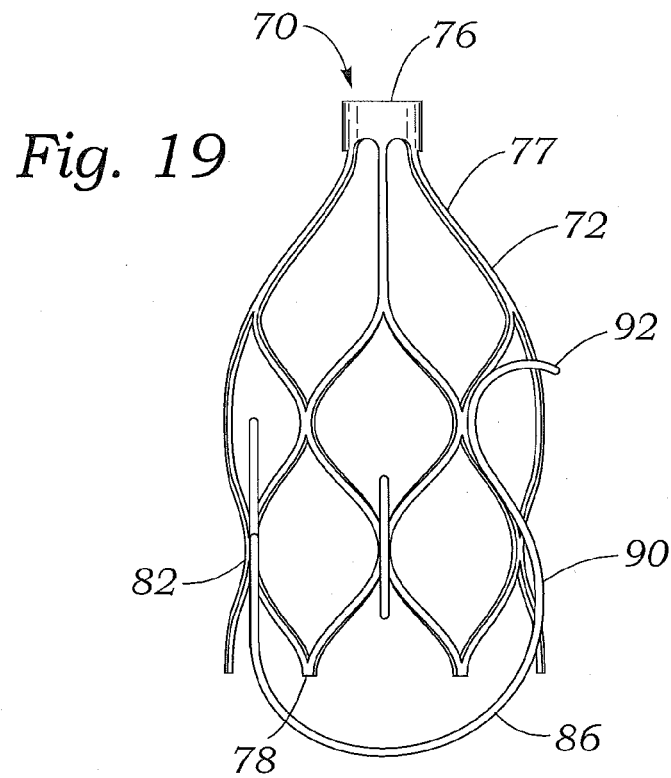
FIG. 19 is a side view of an embodiment similar to that shown in FIG. 16.
Figure 20:
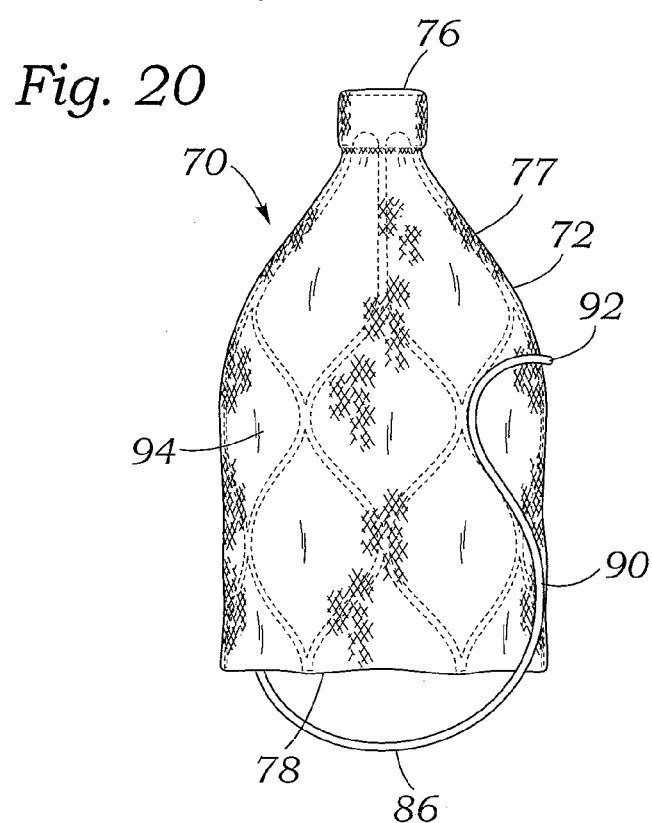
FIG. 20 shows the embodiment of FIG. 19 covered with a fabric layer.

Note that, while FIGS. 16-18 appear to show the end portion 92 of the anchor passing within a portion of the body 72, the end portion 92 actually extends around the outer surface of the body 72, as shown in FIGS. 19 and 20. The position of the end portion 92 in FIGS. 16-18 illustrates the position that the anchor 74 wants to resiliently move toward in the absence of resistance from body 72. When manufactured, the anchor 74 is provided with a pre-bend that causes the end portion 92 to press against the outer surface of the body 72, as shown in FIGS. 19 and 20. This provides the device 70 the ability to apply a strong enough clamping force on a leaflet positioned between the end portion 92 and the body 72, even when the leaflet is very thin.

FIG. 20 also shows a blood-impervious fabric layer 94 covering the body 72 which can prevent blood from flowing through the body 72. The fabric layer can comprise, for example, polyethylene terephthalate (PET) or polyurethane. Any of the spacers described herein (even if shown just as a frame) can include such a blood-impervious fabric layer covering the spacer, which can prevent blood from flowing through the spacer.

The device 70 can be can be deployed from a delivery catheter according to the method illustrated with respect to device 50 in FIGS. 11-15, by releasing the anchor 74 first to create a leaflet-receiving gap between the end portion 92 and the body 72. After positioning a leaflet in the gap, the body 72 can subsequently be freed to self-expand radially toward the end portion 92 to clamp the leaflet between the end portion 92 and the second side of the body 72.

Because the anchor 74 extends around the ventricular end 78 of the body, the first portions 84, 86 can be provided with a larger radius of curvature compared to if the anchor 74 was connected to the body 72 on the same side as the end portion 92. This large radius of curvature of the first portions 84, 86 can provide greater control over the clamping forces between the end portion 92 and the body 72, and provide a more robust and durable anchor configuration, reducing stress concentrations in the anchor 74 and connection points 80, 82. Because the body is acting as a spacer, causing the blood to flow around it, the anchor 74 can pass around the ventricular end 78 of the body without obstructing the flow of blood any more than necessary. Having the anchor members 84, 86 positioned below the ventricular end of the body may not be as desirable in embodiments where the body comprises an annular frame with a prosthetic valve within the annular frame, since the members 84, 86 could restrict the flow of blood through the body to some degree.

Figure 21:
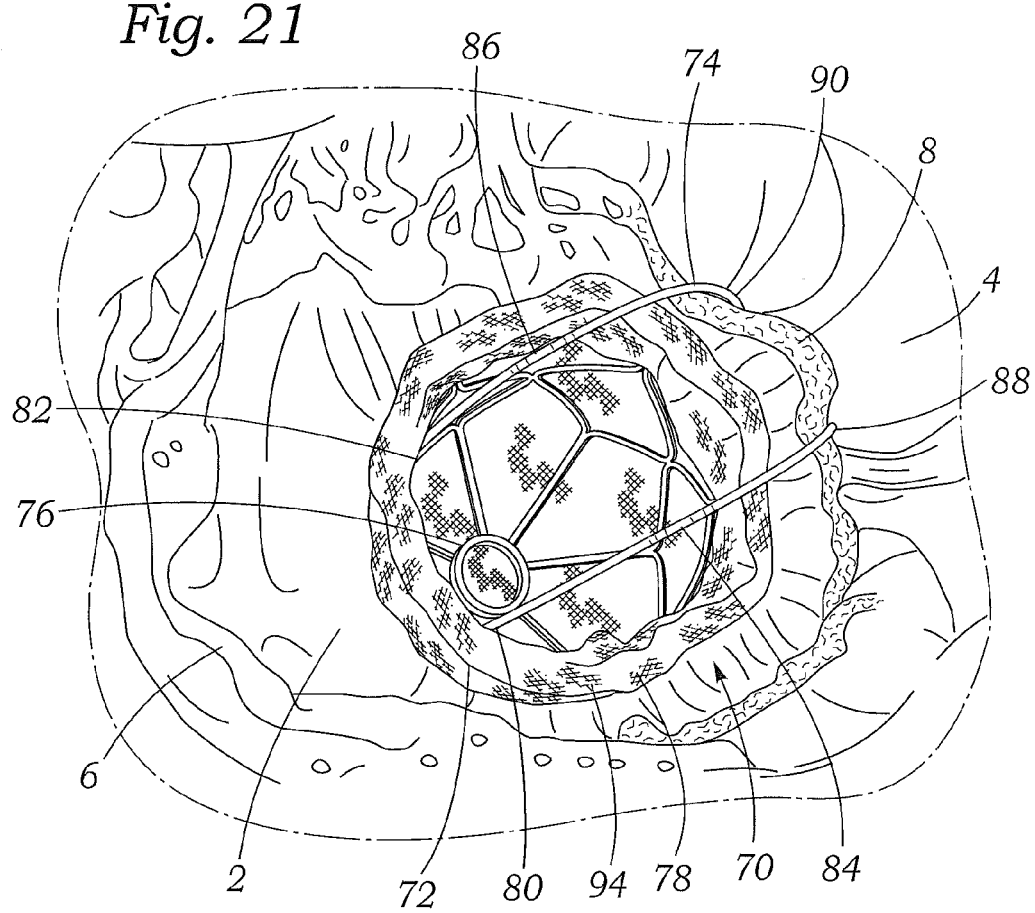
FIG. 21 is a ventricular end view of the embodiment of FIG. 20 implanted at a native mitral valve.

In the case of the device 70, when the device is clipped onto a mitral leaflet between the end portion 92 and the second side of the body 72, a majority of the blood flow passes around the other three sides of the body (i.e., the left, right, and bottom side in FIG. 18). This is illustrated in FIG. 21, which shows a ventricular end view of the device 70 implanted in a mitral orifice with the posterior leaflet 8 captured between the anchor 74 and the body 72. The anterior leaflet 6 is opened away from the body 72 in FIG. 21, allowing blood to flow around three sides of the body during diastole. As shown in FIG. 21, the first members 84, 86 of the anchor 74 extend across the body without blocking the flow of blood around the body. Though not shown, during systole, the anterior leaflet 6 can close around the body 72 and create a seal with the body and the side portions of the posterior leaflet 8 to prevent regurgitation into the left atrium 2. The body 72 is shown in FIG. 21 covered with the blood-impervious fabric 94 that extends around the atrial end 76 of the body and is open on the ventricular end 78 of the body, preventing blood from flowing through the body 72. In some embodiments, the ventricular end 72 can also be covered by the fabric to fully enclose the body and provide improved hemodynamics.

Figure 22:
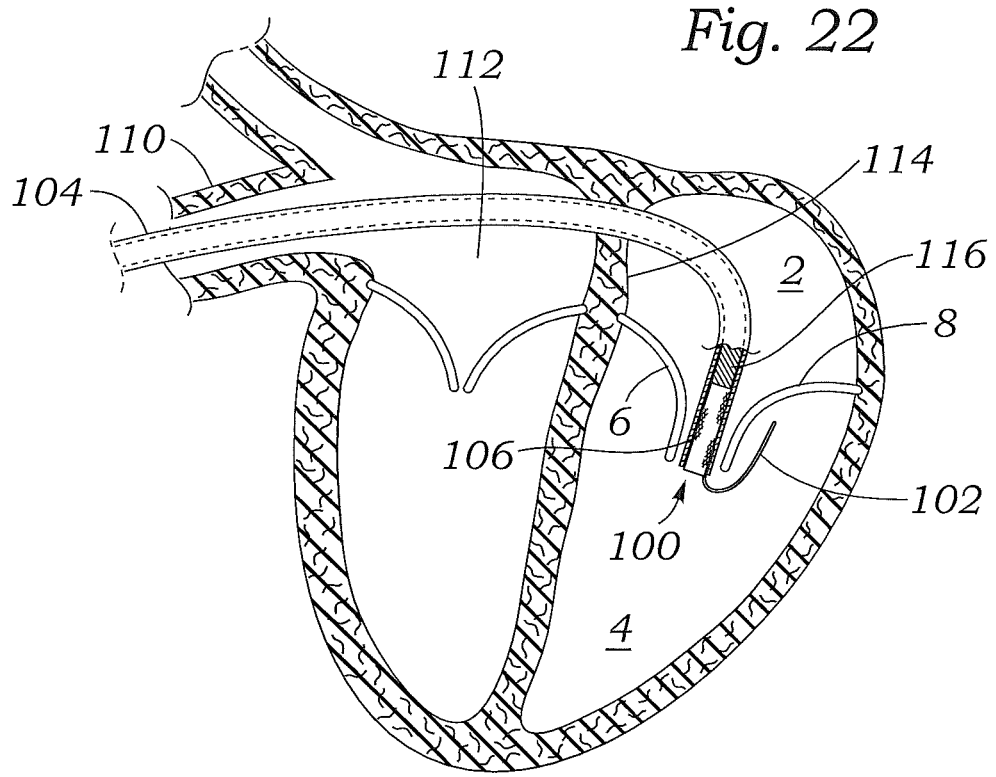
FIG. 22 shows a portion of a human heart with an exemplary sealing device being implanted at the mitral region in a transeptal approach.

The exemplary prosthetic devices disclosed herein can be delivered to the mitral region via plural different approaches. FIG. 22 shows an exemplary prosthetic device 100 having a single anchor 102, being delivered with a catheter 104 via an exemplary transeptal atrial approach. In the approach shown in FIG. 22, the catheter 104 passes through the inferior vena cava 110, the right atrium 112, and through an incision made in the septum 114, to reach the left atrium 2. The distal end portion 106 of the catheter 104 serves as a sheath for containing the prosthetic device 100 in a compressed state during delivery to the heart. The delivery apparatus can further include a pusher member 116 extending coaxially through the catheter 104. Once the catheter enters the left atrium 2, implantation of the device 100 can be performed similar to the methods described in relation to FIGS. 11-21 herein. Alternatively, the prosthetic devices described herein can be implanted via an atrial approach using any of the methods and/or devices described in U.S. Patent Application Publication No. 2011/0137397 in relation to FIGS. 63-67 thereof, or in U.S. Provisional Patent Application No. 61/760,577.

Figure 23:
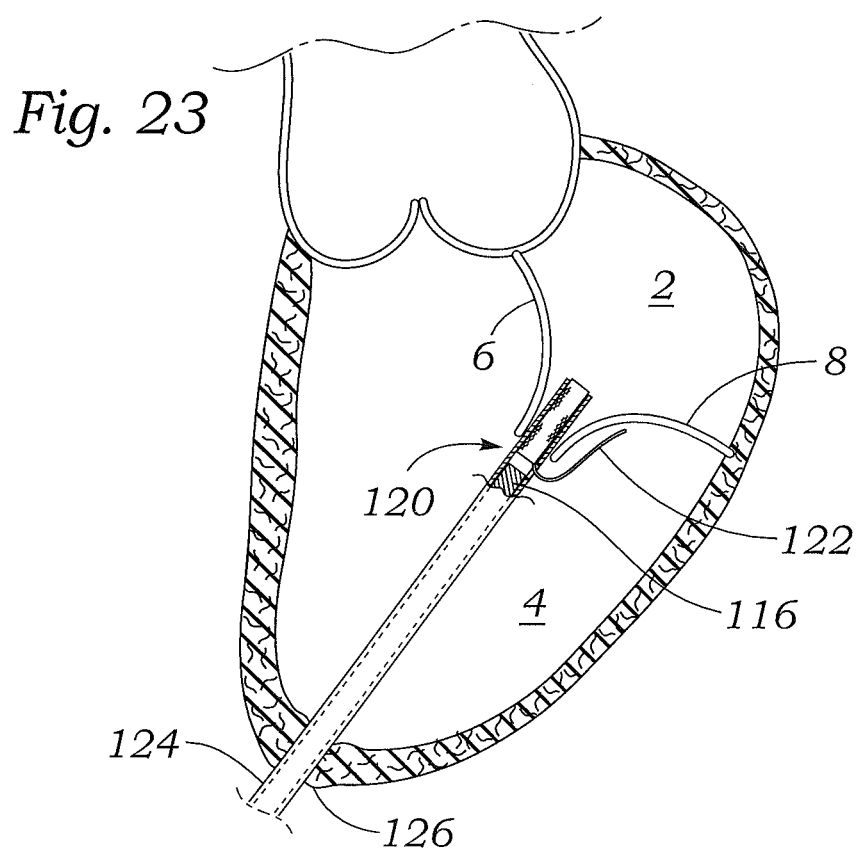
FIG. 23 shows a portion of a human heart with an exemplary sealing device being implanted at the mitral region in a transapical approach.

FIG. 23 shows an exemplary prosthetic device 120 having a single anchor 122, being delivered with a delivery device 124 through the apex 126 of the heart in an exemplary transapical approach. In the transapical approach shown in FIG. 23, the prosthetic device 120 is held in a compressed configuration in a distal end of the delivery device 124 as the delivery device is inserted through an incision in the heart apex 126 and delivered through the left ventricle 4 to the mitral region. The delivery device 124 can have features that allow the anchor 122 to radially expand out of the delivery device 124 and away from the still-compressed body of the prosthetic device 120, as shown in FIG. 23, to capture one of the native mitral leaflets 6 or 8. For example, the delivery device 124 can have an outer sheath configured to release the anchor 122 while the body of the prosthetic device is held in a compressed state in an inner sheath, such as by providing a slot in the distal end portion of sheath 124 through which the anchor 122 can extend. In some embodiments, the delivery device 124 can be similar to the delivery device 2000 described in U.S. Patent Application Publication No. 2011/0137397 (for example, with only one of the slots 2028 instead of two), and can be used to implant the prosthetic device 120 via methods similar to those described therein in relation to FIGS. 49-62 thereof. The delivery device 124 can also be similar to the delivery devices described in U.S. Provisional Patent Application No. 61/760,577, and can be used to implant prosthetic devices via methods similar to those described therein.

Figure 24:
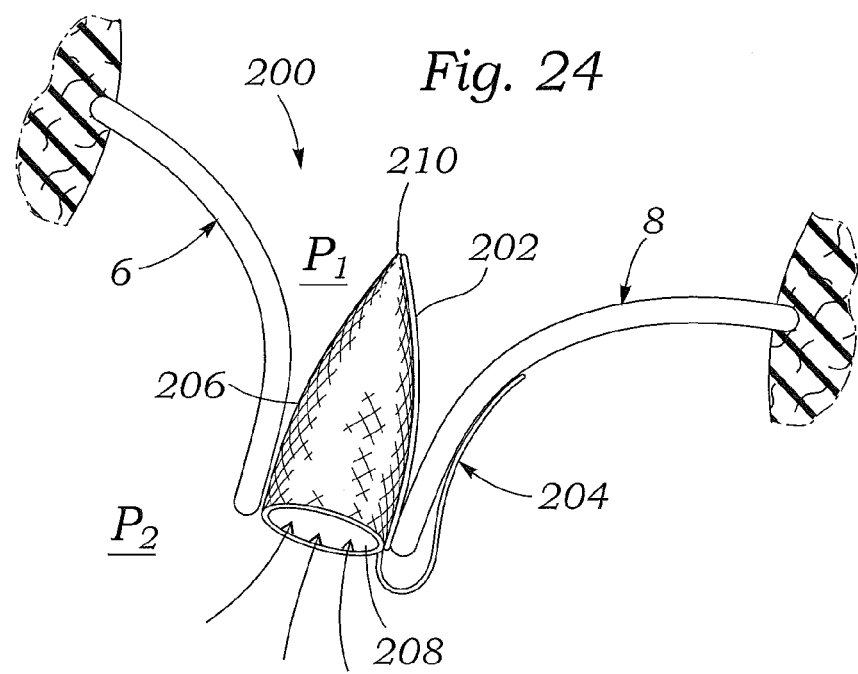
FIG. 24 shows a human heart with an exemplary prosthetic device attached to a native mitral leaflet.

FIG. 24 shows an exemplary prosthetic device 200 that is configured to inflate with blood and expand radially during systole and to collapse radially during diastole. The device 200 can comprise a structural portion 202, an anchor 204, and an inflatable portion, or parachute, 206 having an annular cross-sectional profile. The structural portion 202 can comprise a rigid member or frame that supports one side of the parachute 206. The anchor 204 can comprise an extension of the structural member 202 or a separate member coupled to the structural member and is configured to attach the device 200 to one of the native mitral leaflets, such as the posterior native leaflet as shown in FIG. 24, by capturing the leaflet between the anchor 204 and the structural portion 202. The parachute 206 can comprise a flexible, blood-impermeable material, such as PET fabric or the like. The parachute 206 has an open lower end 208 and a closed upper end 210.

During systole, as illustrated in FIG. 24, higher pressure in the left ventricle relative to the left atrium forces blood from the left ventricle into the open lower end 208 of the parachute. The increased pressure in the parachute (labeled $P_2$ in FIG. 24) exceeds the pressure in the left atrium (labeled $P_1$ in FIG. 24), causing the parachute to inflate with blood and to expand radially and upwardly. At the same time, the native leaflets 6, 8 are caused to collapse toward each other. The device 200 moves along with the leaflet to which it is attached and the other leaflet moves toward the expanding parachute 206. When fully inflated, the parachute 206 can seal the gap between the two native mitral leaflets 6, 8 and prevent or reduce mitral regurgitation.

During diastole (not shown), $P_1$ exceeds $P_2$ causing the parachute 206 to deflate and collapse toward the structural portion 202. At the same time, the two native leaflets 6, 8 are pushed apart. This allows blood to flow from the left atrium to the left ventricle with minimal obstruction by the collapsed parachute 206.

In some embodiments, the device 200 can comprise additional structural elements. For example, some embodiments can comprise longitudinal splines that extend from the upper end 210 to the lower end 208 to provide longitudinal rigidity to the parachute without impeding expansion/contraction in the radial direction, much like a common umbrella. In some embodiments, the device 200 can comprise a structural member at the lower opening 208 to prevent the lower opening from fully closing during diastole, such that blood can more easily enter the lower opening at the beginning of systole. In some embodiments, the device 200 can comprise a biased portion that urges the lower opening 208 toward an opened position. The biased portion can comprise a spring mechanism, resiliently flexible members, or other mechanisms. In some embodiments, the device 200 can further comprise an atrial portion that extends from or adjacent to the upper end 210 and contacts the atrial walls and/or the atrial side of the leaflet to which the device is attached. The atrial body can help secure the device within the mitral orifice and can prevent movement toward the left ventricle. The atrial body can comprise a separate component or an extension of the structural member 202. The atrial body can be configured like the atrial bodies 26A, 26B or 26C described above, or can have other configurations.

Figure 25:
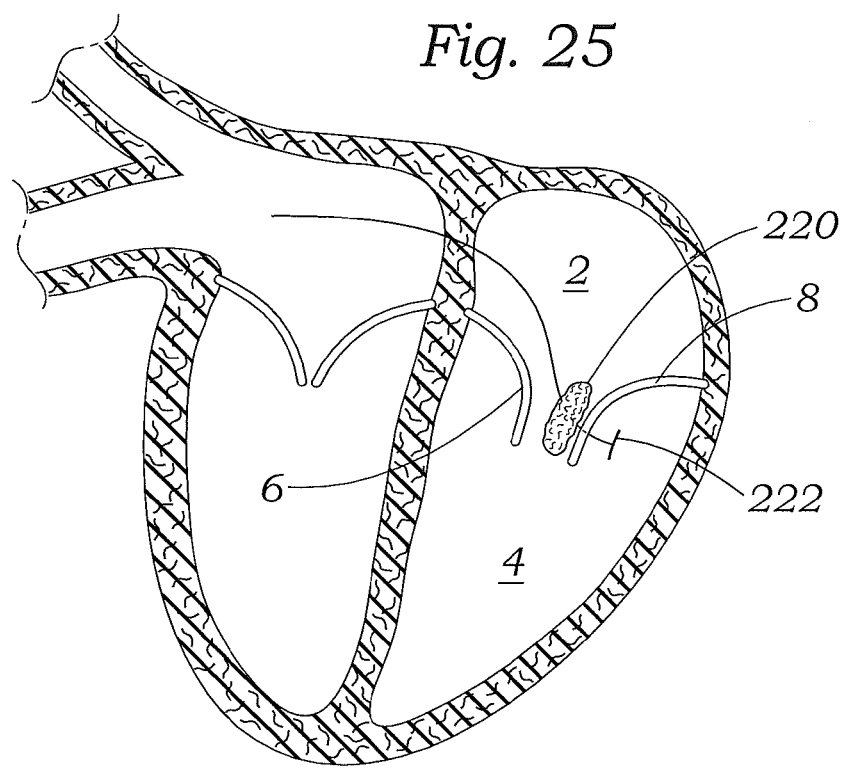
FIG. 25 shows an exemplary prosthetic device being coupled to a native mitral leaflet in a transeptal approach.
Figure 26:
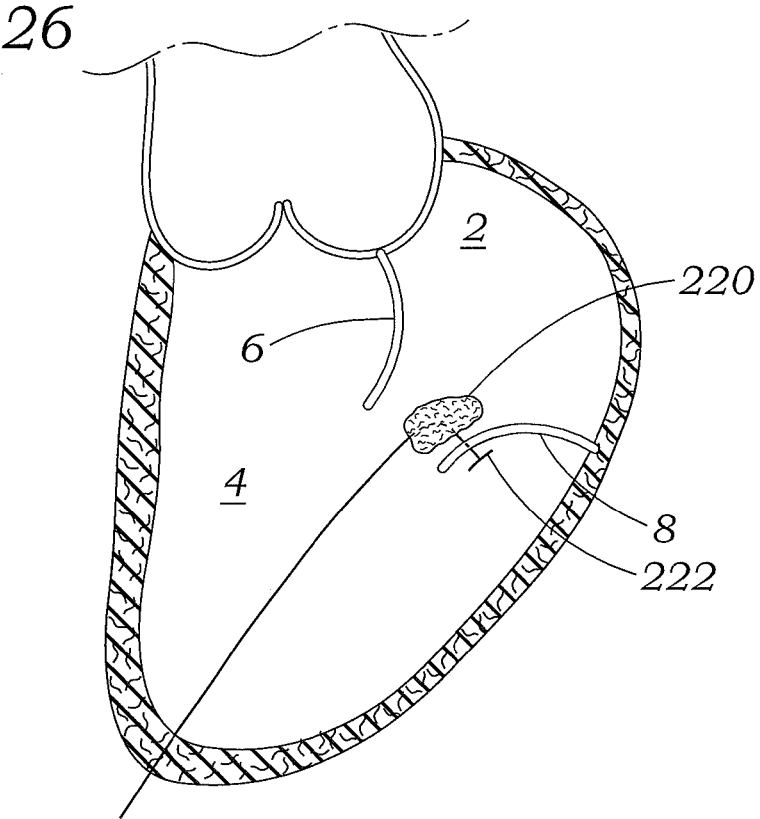
FIG. 26 shows an exemplary prosthetic device being coupled to a native mitral leaflet in a transapical approach.

FIGS. 25-28 show a prosthetic spacer 220 according to another embodiment, wherein the spacer 220 is coupled to one of the native leaflets using, for example, sutures. The spacer 220 can be formed from any of various suitable materials, including bio-compatible materials such as pericardial tissue, polymers, sponge, or a gel or saline filled structure such as a balloon. The material composition of the spacer 220 can be selected to increase desirable characteristics of the spacer 220, such as performance, durability, promotion of native tissue growth, etc. The spacer 220 can be formed in any of various suitable shapes, such as a rectangle, a semi-elliptical ring or generally u-shape, or a semi-ellipse. As shown in FIG. 25, the spacer 220 can be sutured to the posterior leaflet 8 using sutures 222 via a transeptal approach, and as shown in FIG. 26, the spacer 220 can be sutured to the posterior leaflet 8 using sutures 222 via a transapical approach. In use, the opposite leaflet (the anterior leaflet in the illustrated embodiment) can coapt against the spacer 220 to prevent or minimize regurgitation.

Figure 27:
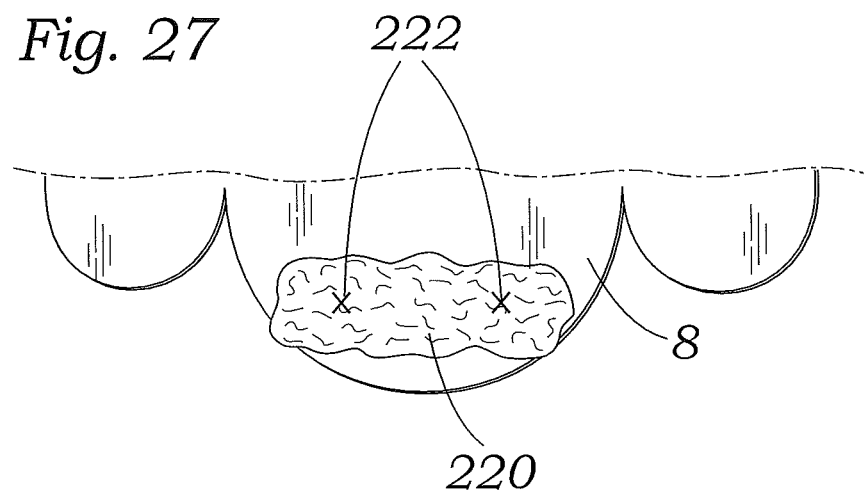
FIGS. 27 and 28 show another exemplary prosthetic device being coupled to a native mitral leaflet.

FIG. 27 shows the spacer 220 after it has been sutured to the native posterior leaflet 8. As shown, two sutures 222 can be sufficient to couple the spacer 220 to the leaflet 8. The sutures 222 can be positioned as shown, with one suture 222 at either end of the spacer 220, which spans across the leaflet 8. In alternative embodiments, additional or fewer sutures can be used, and the sutures can be situated in alternative locations on the spacer 220 and/or on the leaflet 8.

Figure 28:
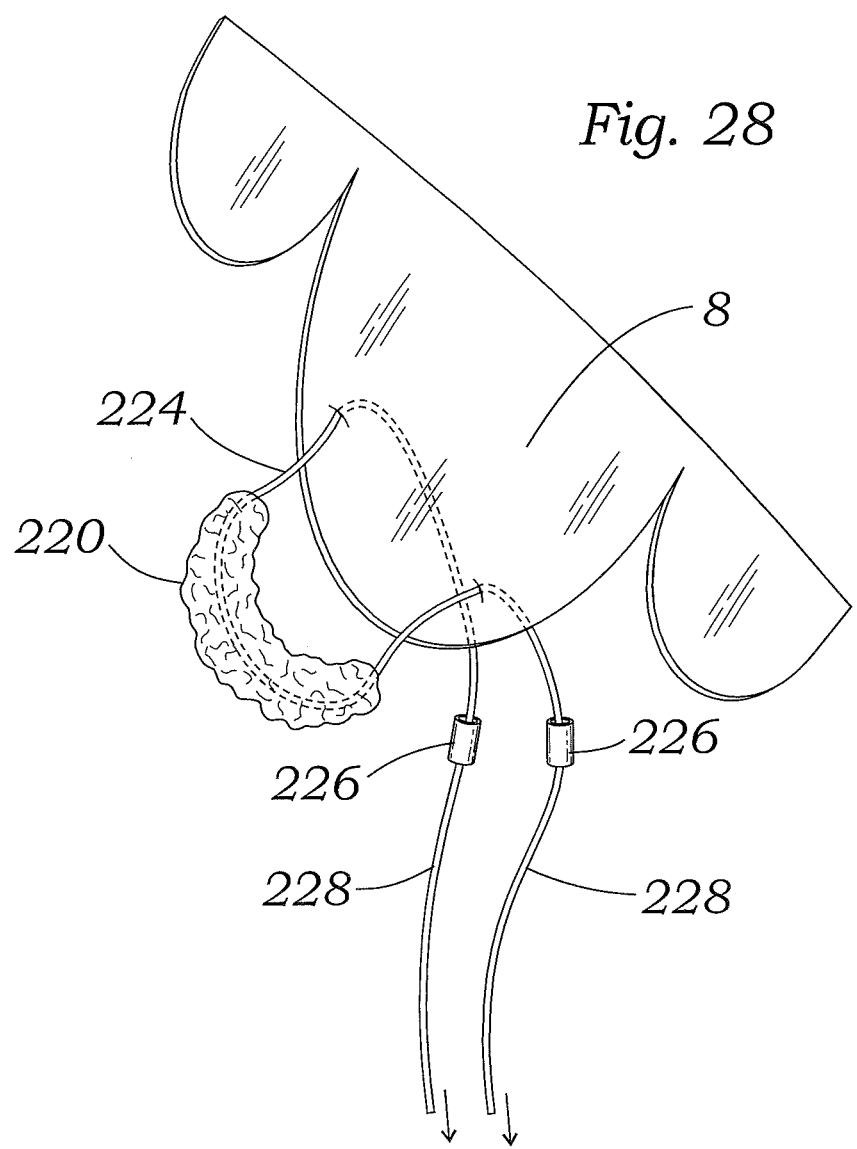

FIG. 28 shows the spacer 220 being coupled to the posterior native leaflet 8 using a length of elongated material 224 and a pair of slidable locking devices 226. The elongated material 224 can comprise, for example, a length of thread or suture material, or a metal or polymeric wire, or other material suitable for suturing, such as biological tissue. In the illustrated embodiment, a single strand of material 224 is used, although in alternative embodiments, two or more strands 224 can be used to couple the spacer 220 to the native leaflet 8. In order to couple the spacer 220 to the native posterior leaflet 8, one or both of the slidable locking devices 226 can be guided along the strand of material 224 toward the native leaflet 8, thereby decreasing the length of the strand 224 between the locking devices 226 until the spacer 220 is held firmly against the leaflet 8 in a desired deployed configuration. Because the locking devices 226 are positioned behind the posterior leaflet 8 in this configuration (that is, they are located between the native leaflet 8 and the wall of the left ventricle 4), the potential for interference between the locking devices 226 and the coaptation area of the leaflets 6, 8 is minimized. Once the spacer 220 is situated in this configuration, any excess material 228 can be trimmed to prevent interference of the material 224 with the operation of the heart valve. The locking devices 226 can be configured to be slid or passed over a suture in one direction and resist movement in the opposite direction. Examples of locking devices (also referred to as suture securement devices) that can be implemented in the embodiment of FIG. 28 are disclosed in co-pending application Ser. No. 13/938, 071, filed Jul. 9, 2013, which is incorporated herein by reference.

FIGS. 25-28 show one spacer 220 coupled or secured to the posterior leaflet 8. In alternative embodiments, a spacer 220 can be coupled as described above to the anterior leaflet 6 in place of or in addition to the spacer 220 coupled to the posterior leaflet 8. Except where physically impossible, any of the embodiments described herein can be sutured to native tissue as described above with reference to spacer 220, rather than or in addition to being clipped to the native leaflets using one or more anchors.

By anchoring a prosthetic mitral device to one of the mitral leaflets, as disclosed herein, instead of anchoring the device to the walls of the left ventricle, to the walls of the left atrium, to the native valve annulus, and/or the annulus connection portions of the native leaflets, the device anchorage is made independent of the motions of the ventricular walls and atrial walls, which move significantly during contractions of the heart. This can provide a more stable anchorage for a prosthetic mitral device, and eliminate the risk of hook-type or cork screw-type anchors tearing or otherwise causing trauma to the walls of the left ventricle or left atrium. Furthermore, the device body can be held in a more consistent position with respect to the mitral leaflets as the leaflets articulate, eliminating undesirable motion imparted on the device from the contraction motions of the left ventricle walls and left atrium walls. Anchoring to a mitral leaflet can also allow for a shorter body length compared to devices having other anchorage means.

Leaflet Extension

Figure 29:
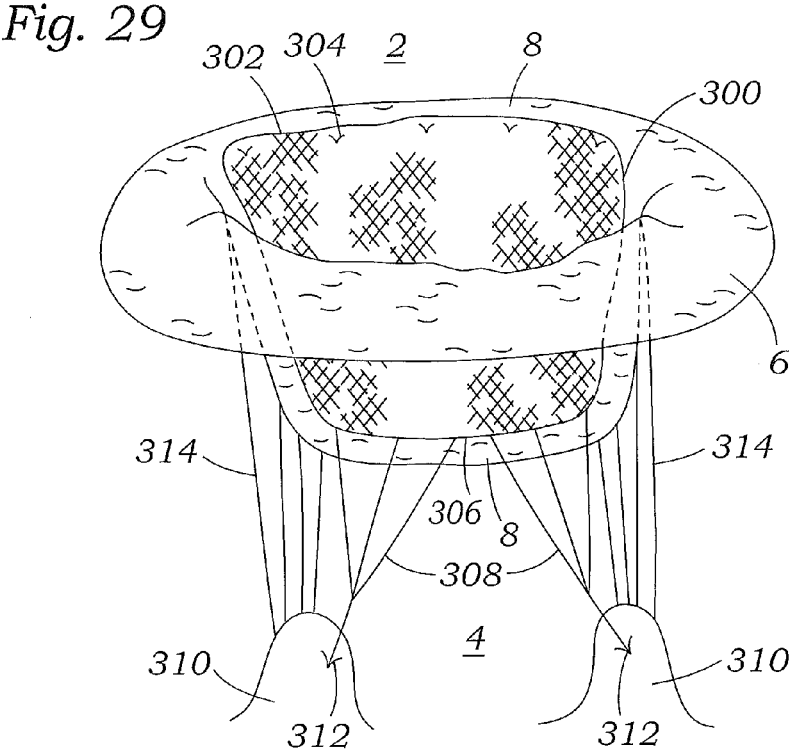
FIGS. 29-31 show an exemplary prosthetic device attached to the mitral valve region of a human heart.

FIG. 29 shows another exemplary prosthetic device 300 implanted at the mitral valve region for treating regurgitation. The device 300 comprises a strong, flexible sheet of blood-impermeable material. The device 300 has an upper end 302 that is secured to the mitral annulus and/or the region of a mitral valve leaflet adjacent to the mitral annulus. The portion of the device 300 extending away from this upper end portion 302 is a free end portion of the device 300. In the illustrated example, the upper end 302 is attached to the mitral annulus above the posterior leaflet 8. In other examples, the arrangement can be reversed with the device 300 secured to the anterior leaflet 6. The device 300 can be secured to the native tissue by various means, such as via suturing or via barbed anchors or microanchors 304. The upper end 302 of the device 300 can be wider than the free end portion of the device 300, thus the device 300 can have a generally trapezoidal shape.

Figure 30:
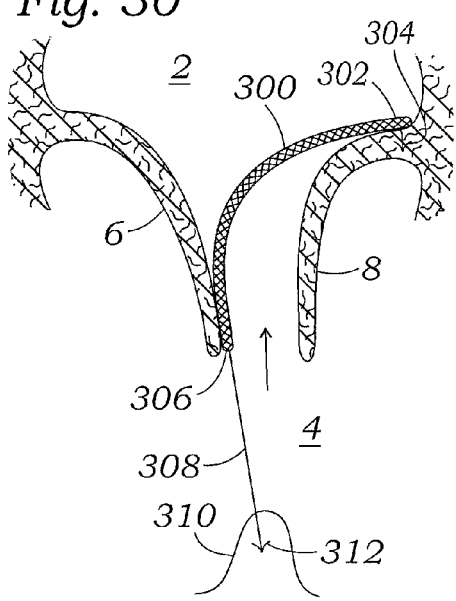
Figure 31:
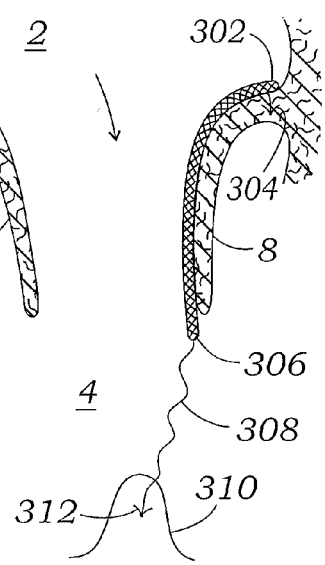

In FIG. 29, the lower end of the anterior leaflet 6 is not shown in order to show the lower end of the posterior leaflet 8 and the lower end 306 of the device 300 extending downwardly through the mitral orifice and into the left ventricle 4. The lower end 306 of the device can be shorter, longer, or about the same length as the leaflet to which it is attached. As shown in FIGS. 30 and 31, the lower end 306 of the device in the illustrated embodiment extends below the lower end of the posterior leaflet during diastole (FIG. 31), and extends short of the lower end of the anterior leaflet 6 during systole (FIG. 30). The lower end 306 can be tethered to a location in the left ventricle 4. For example, the lower end 306 can be tethered to the papillary muscle heads 310 via tethers 308 and anchors 312, as shown, (in a manner similar to the way in which the native chordae tendineae 314 tether the native leaflet 8 to the papillary muscles 310), or can be tethered to the apex of the left ventricle.

During systole, as shown in FIG. 30, the device 300 inflates or fills with blood from the left ventricle 4 and expands laterally toward the anterior leaflet 6. This causes the lower portion of the device 300 to seal against the anterior leaflet 6, blocking the flow of blood back into the left atrium 2. The lateral edges of the device 300 can seal between the two native leaflets adjacent to the commissures where the native leaflets still naturally coapt with each other. The tethers 308 prevent the lower end 306 of the device 300 from moving toward and/or into the left atrium 2 and thereby breaking the seal with the anterior leaflet 6. Thus, the device 300 augments the native posterior leaflet and helps seal the mitral orifice in the case where the native leaflets 6, 8 do not otherwise not fully coapt and allow regurgitation between them.

During diastole, as shown in FIG. 31, high pressure in the left atrium 2 forces the device 300 to collapse against the posterior leaflet 8, allowing blood to flow into the left ventricle 4 with minimal obstruction from the device 300.

Figure 32:
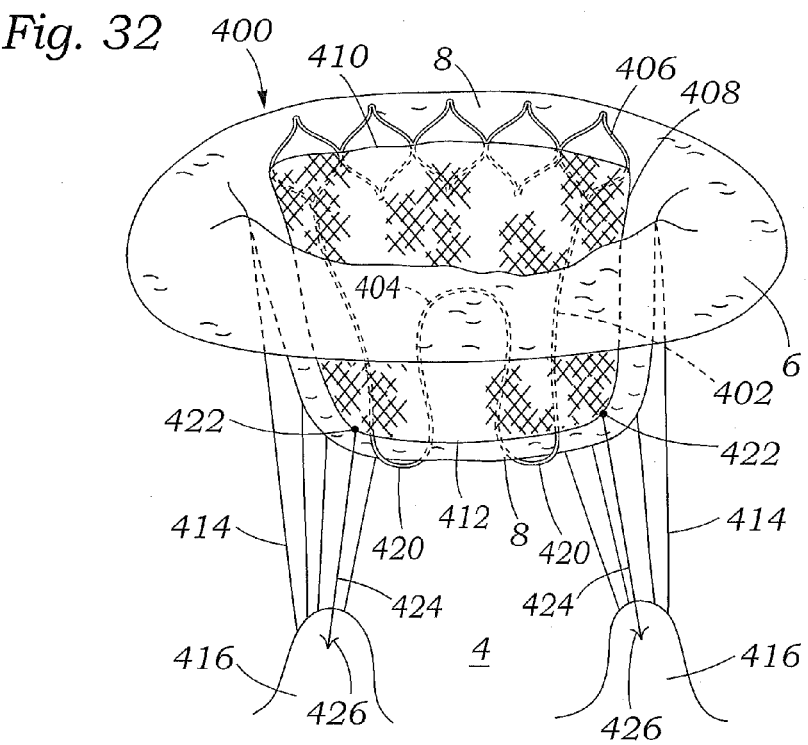
FIGS. 32-34 show another exemplary prosthetic device attached to the mitral valve region of a human heart.

FIG. 32 shows another exemplary prosthetic device 400 implanted at the mitral valve region for treating mitral regurgitation. The device 400 comprises a rigid frame 402 (e.g., a metal frame) that clips around the posterior leaflet 8 with an anchor portion 404 being positioned behind the posterior leaflet 8 and an atrial portion 406 being positioned along the atrial surface of the mitral annulus and/or the portion of the posterior leaflet adjacent to the annulus. The frame 402 can secure the device 400 to the posterior leaflet 8 without sutures or other tissue puncturing elements like the anchors 304 in FIGS. 29-31. The device 400 also can be implanted on the anterior leaflet 6. The device 400 further comprises a strong, flexible sheet 408 of blood-impermeable material, like the device 300. An upper end 410 of the sheet 408 can be secured to the frame 402 at or near the atrial portion 406. The portion of the sheet 408 extending away from this upper end portion 410 is a free end portion of the sheet 408.

Figure 33:
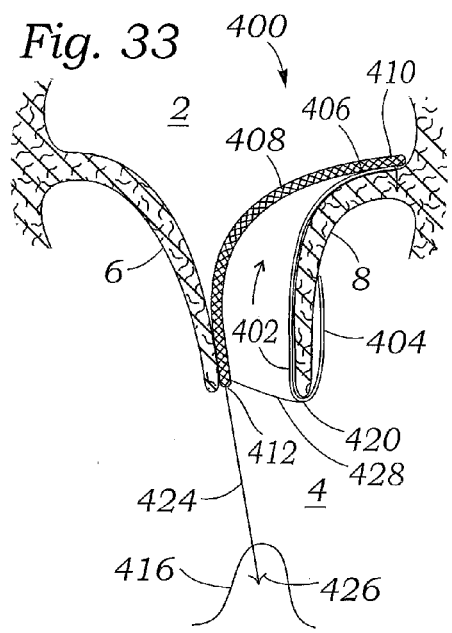
Figure 34:
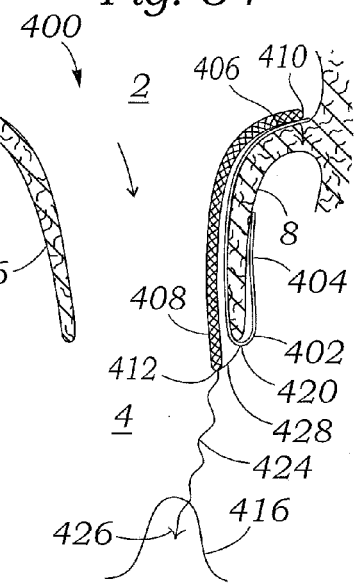

In FIG. 32, the lower end of the anterior leaflet 6 is not shown in order to show the lower end of the posterior leaflet 8 and the lower portions of the device 400 extending downwardly through the mitral orifice and into the left ventricle 4. The lower end 412 of the sheet 408 can be shorter, longer, or about the same length as the lower end of the leaflet to which it is attached. As shown in FIGS. 33 and 34, the lower end 412 of the sheet 408 in the illustrated embodiment extends below the lower end of the posterior leaflet during diastole (FIG. 34), and extends short of the lower end of the anterior leaflet 6 during systole (FIG. 33). The lower end 412 can be tethered to a location in the left ventricle 4 and/or can be tethered to one or more points 420 near the lower end of the frame 402 (both tethering means are shown in FIGS. 33 and 34, though one can be used without the other). For example, in some embodiments, the lower end 412 of the sheet 408 can be tethered to the papillary muscle heads 416 via tethers 424 and anchors 426 (in a manner similar to the way in which the native chordae tendineae 414 tether the native leaflet 8 to the papillary muscles 416), and/or can be tethered to the apex of the left ventricle 4. In other embodiments, the sheet 408 is tethered only to the frame 402 and tethers extending down into the left ventricle 4 are optional. In such embodiments, one or more tethers 428 can extend from adjacent the lower end 412 of the sheet, such as from the lower lateral corners 422, and attach to the lower end of the frame at or near points 420. In some embodiments, the sheet 408 can adopt a three dimensional curvature when inflated, with the lower corners being held closer to the lower end of the frame 402 while an intermediate portion of the lower edge 412 is allowed to billow out (somewhat like a spinnaker sail) further toward the anterior leaflet 6 to create a seal.

During systole, as shown in FIG. 33, the sheet 408 inflates or fills with blood from the left ventricle 4 and expands laterally toward the anterior leaflet 6. This causes the lower portion of the sheet 408 to seal against the anterior leaflet 6, blocking the flow of blood back into the left atrium 2. The lateral edges of the sheet 408 can seal between the two native leaflets adjacent to the commissures where the native leaflets naturally coapt with each other. Thus, the device 400 augments the native posterior leaflet and helps seal the mitral orifice in the case where the native leaflets 6, 8 do not otherwise not fully coapt and allow regurgitation between them.

During diastole, as shown in FIG. 34, high pressure in the left atrium 2 forces the sheet 408 to collapse against the posterior leaflet 8, allowing blood to flow into the left ventricle 4 with minimal obstruction from the device 400.

Figure 35:
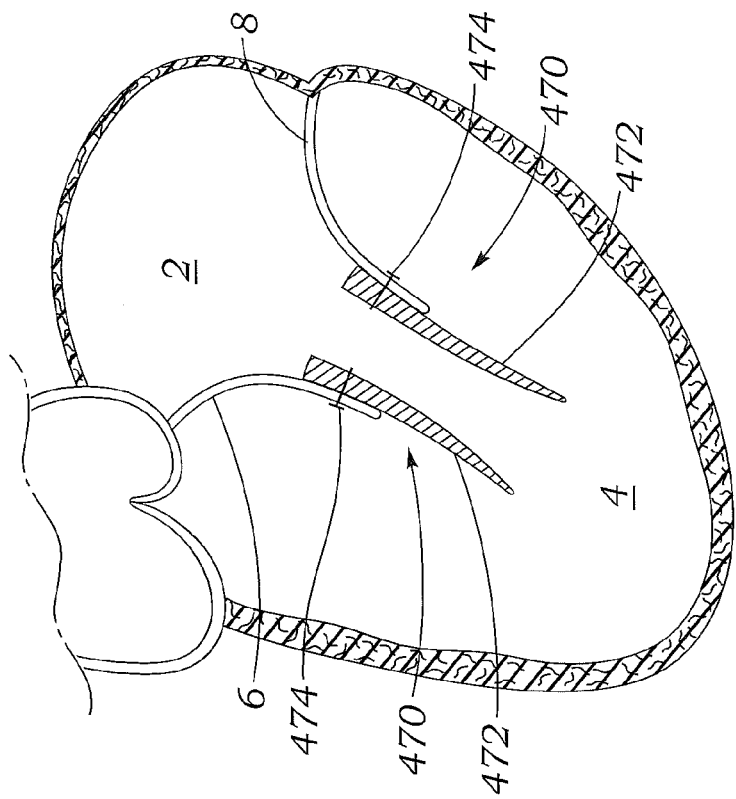
FIG. 35 shows two exemplary prosthetic devices, each being coupled to a respective one of the native mitral valve leaflets.
Figure 36:
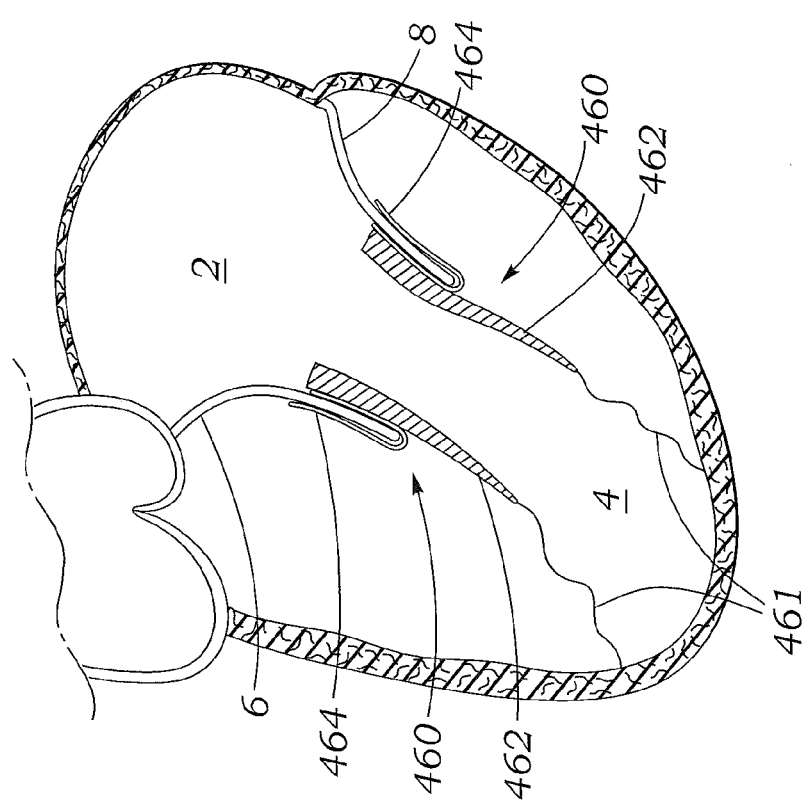
FIG. 36 shows two exemplary prosthetic devices, each being coupled to a respective one of the native mitral valve leaflets.

FIGS. 35 and 36 show embodiments of prosthetic devices 460, 470 which can be used to extend the effective length of the native leaflets 6, 8. As shown in FIG. 35, a prosthetic device 460 can include a body 462 and a clip 464 for clipping the device 460 to one of the anterior or posterior native leaflets 6, 8. As shown in FIG. 36, a prosthetic device 470 can include a body 472 and one or more sutures 474 for coupling the device 470 to one of the anterior or posterior native leaflets 6, 8. In use, the devices 460, 470 have free end portions extending away from the native leaflets which extend the effective length of the native leaflets, thereby increasing the chance of and extent of coaptation between them, as described more fully below. The bodies 462, 472 can comprise a material which is stiff enough to reduce the chance of leaflet prolapse, and flexible enough to increase the extent of leaflet coaptation. Suitable materials can include, for example, biological materials such as pericardial tissue, goretex, silicone, polyurethane, or other polymeric materials. FIG. 35 shows that a device 460 can be used on each of the anterior and posterior native leaflets 6, 8, and FIG. 36 shows that a device 470 can be used on each of the anterior and posterior native leaflets 6, 8, but in alternative embodiments, only one such device can be used, or one device 460 and one device 470 can be used. FIG. 35 shows that tethers 461 can be used to tether free end portions of the bodies 462 to locations in the left ventricle, thus reducing the chances of prolapse of the prosthetic devices 460 during systole. The tethers 461 are optional, and can be used in a similar fashion in combination with the devices 470, 500, 502, or any other suitable devices described herein.

Figure 37:
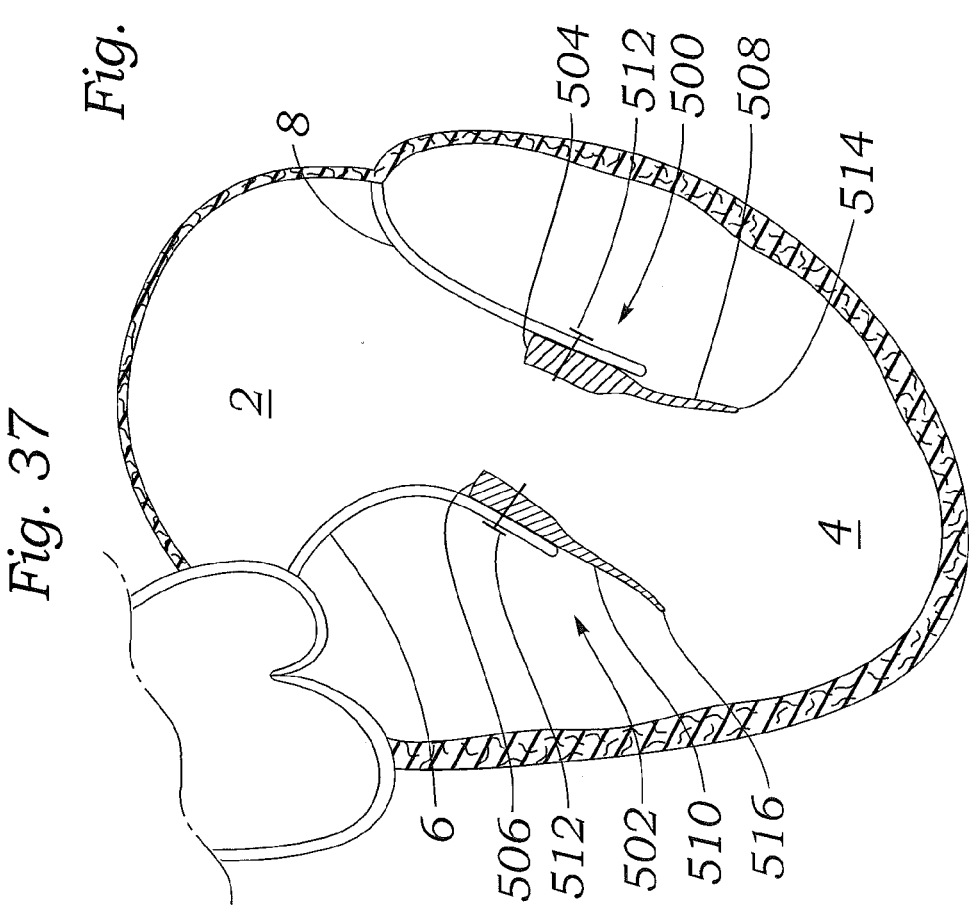
FIG. 37 shows two exemplary prosthetic devices, each being coupled to a respective one of the native mitral valve leaflets.

FIG. 37 shows exemplary prosthetic devices 500, 502 which combine features of the prosthetic spacers and the leaflet extensions described above. Prosthetic device 500 is shown coupled to the posterior native leaflet 8 while the prosthetic device 502 is shown coupled to the anterior native leaflet 6. The prosthetic devices 500, 502 include relatively thick upper portions 504, 506, which function in a manner similar to the prosthetic spacers described above, and relatively thin, elongate free end portions 508, 510, which function in a manner similar to the devices 300, 400, described above. The free end portions 508, 510 can have respective distal end portions 514, 516, which represent the effective distal ends of the extended leaflets.

In use, the free end portions 508, 510 extend the effective length of the respective leaflets, and can facilitate initiation of leaflet coaptation during ventricular systole. During systole, the leaflets are urged toward one another due to the pressures extant in the left ventricle and left atrium. Due to the extended effective length of the leaflets, the end portions 514, 516 are more likely to coapt than were the ends of the native leaflets without the extensions. Once coaptation is initiated, and thus blood flow from the left ventricle to the left atrium at least partially impeded, the pressure in the left ventricle can increase, further increasing the pressure differential between the left ventricle and the left atrium and urging the leaflets 6, 8, further toward one another.

As a result, the portions of the leaflets 6, 8, and their respective extensions 502, 500 which coapt, increases (both in the direction from the end portions 514, 516 toward the left atrium 2, and from the locations of the devices 500, 502, toward the commissure points of the mitral valve), leading to a cycle of increasingly impeded blood flow, increased pressure differential, and increased coaptation of the leaflets. Thus, by facilitating initiation of coaptation, the free end portions 508, 510 can help to reduce regurgitation of blood from the left ventricle to the left atrium during ventricular systole. Further, the upper portions 504, 506 can further help to prevent regurgitation in the manner described above with respect to prosthetic device 10. In cases where the native leaflets 6, 8, do not experience sufficient coaptation to prevent regurgitation, the relatively thick upper portions 504, 506, can help to increase their coaptation and thereby reduce regurgitation.

FIG. 37 shows that the devices 500, 502 can be sutured to the native leaflets 8, 6, with sutures 512, but in alternative embodiments, the devices 500, 502 can be clipped to the native leaflets 8, 6, as described above. In alternative embodiments, only one of the devices 500, 502 can be used rather than both.

Spacers Having Plural Anchors

In some embodiments, prosthetic devices can include a body and a plurality of anchors such that the body can be clipped to more than one leaflet. Such embodiments can be used to effectively couple two or more leaflets to one another. Thus, such a device can be used to bring native leaflets closer to one another and restrict their mobility in order help increase the chance of or extent of coaptation between the leaflets.

FIGS. 38-41 show a prosthetic spacer 600 having a body 602, a first anchor 604 and a second anchor 606. The body 602 and anchors 604, 606 can be fabricated from any of various suitable materials, and the body is desirably made from a relatively compressible material so that its profile can be reduced for delivery into a patient's heart within a delivery catheter. Alternatively, the body 602 can be inflatable (e.g., to be inflated with a fluid such as saline or a curing epoxy or polymer) or otherwise expandable (e.g., it can be fabricated from a frame comprising a self-expanding material such as Nitinol) such that the cross section of the body 602 can be reduced for delivery into a patient's heart and then expanded to a final, deployed configuration therein. An inflatable spacer can be particularly advantageous because it can allow enhanced customization of the spacer, and can allow fine control over the final, deployed size and configuration of the spacer.

Figure 38:
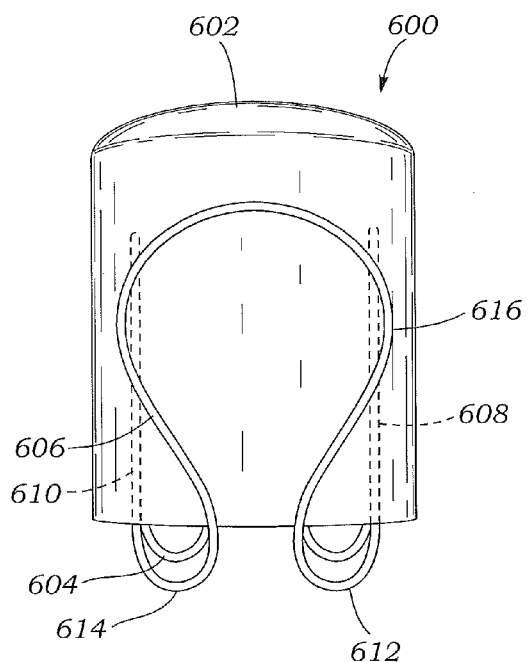
FIGS. 38-41 show an exemplary prosthetic device having two anchors.
Figure 39:
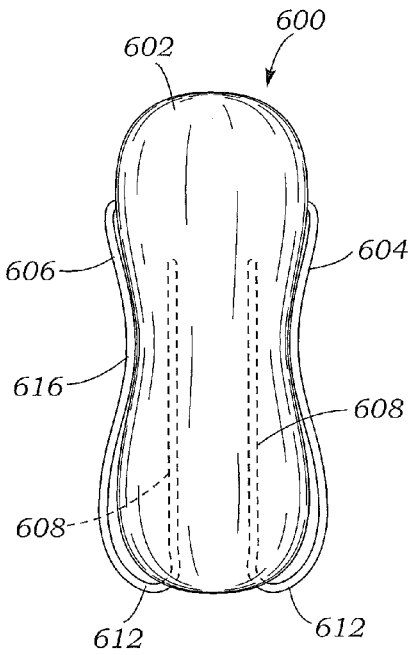

FIGS. 38 and 39 show that the anchors can have similar structures. Each anchor 604, 606 can be made from a single piece of relatively rigid metallic material (e.g., an elongated wire) which can include first and second inner portions 608, 610, first and second bottom portions 612, 614, and a main loop portion 616 extending between and connecting the upper ends of the bottom portions 612, 614. The inner portions 608, 610 can be coupled rigidly to the inside of the body 602. The inner portions 608, 610 can extend downwardly out of the lower end of body 602 to the respective bottom portions 612, 614, which can each curve upwardly around the lower end of the body 602 to meet the main loop portion 616.

Figure 40:
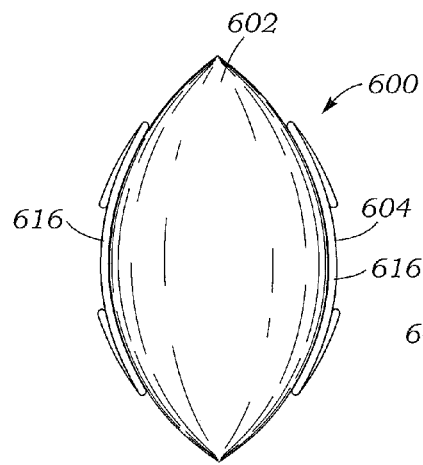
Figure 41:
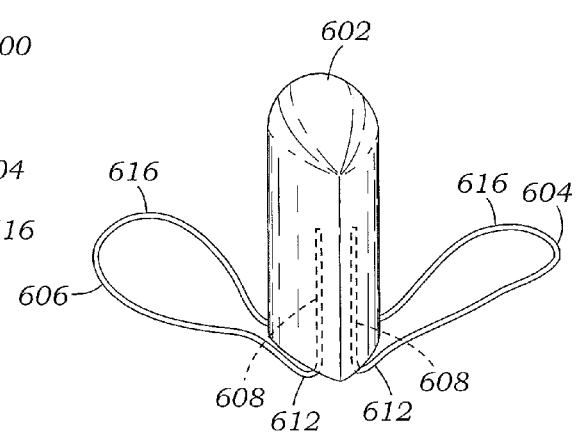

FIGS. 39 and 40 show that the structure of the anchors 604, 606, and their connections to the body 602, biases the main loop portions 616 of the anchors 604, 606, into contact with the sides of the body 602. Thus, in use, the spacer 600 can be clipped to the anterior and posterior native leaflets 6, 8, with one of the leaflets 6, 8 clipped between the anchor 604 and the body 602, and the other of the leaflets 6, 8, clipped between the anchor 606 and the body 602. FIG. 41 shows that the anchors 604, 606 can be splayed apart so that gaps exist between the anchors 604, 606, and the body 602. Thus, the spacer 600 can be introduced into the region of a patient's native mitral valve in a closed configuration with the anchors 604, 606 against the side of the body 602 (FIGS. 38-40). The anchors 604, 606 can then be splayed apart or expanded into an open configuration (FIG. 41) so the spacer can be positioned with the native leaflets 6, 8, in the gaps between the anchors 604, 606 and the body 602, after which the anchors 604, 606 can be allowed to return to the closed configuration under their own resiliency to capture the leaflets 6, 8, and clip the spacer 600 thereto.

Figure 42:
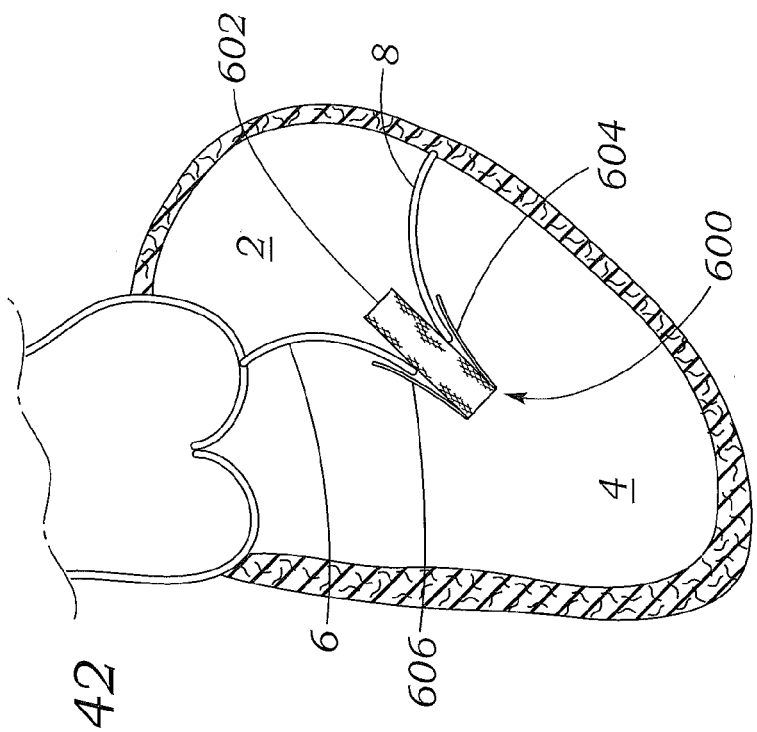
FIG. 42 shows an exemplary prosthetic device having two anchors, coupled to both of the native mitral valve leaflets.
Figure 43:
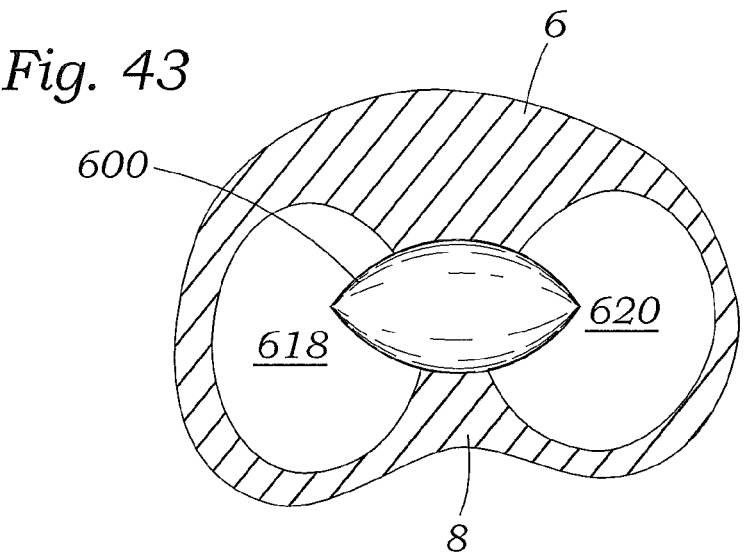
FIG. 43 shows an exemplary prosthetic device having two anchors, coupled to both of the native mitral valve leaflets, from an atrial view.

FIG. 42 shows that in use, the prosthetic spacer 600 can be clipped to the posterior native mitral valve leaflet 8 using the first anchor 604, as described above with regard to prosthetic spacer 10 and shown in FIG. 1, and can be clipped to the anterior native mitral valve leaflet 6 using the second anchor 606, as described above with regard to prosthetic spacer 10 and shown in FIG. 2. FIG. 43 shows that when the prosthetic spacer 600 is clipped to both of the leaflets 6, 8, (e.g., at the A2 and P2 regions of the leaflets, as identified by Carpentier nomenclature) it brings them together, decreasing the overall area of the mitral valve orifice, and dividing the mitral valve orifice into two orifices 618, 620 during diastole. Thus, the area through which mitral regurgitation can occur is reduced, leaflet coaptation can be initiated at the location of the spacer 600, and the leaflets can fully coapt more easily, thereby preventing or minimizing mitral regurgitation.

Figure 44:
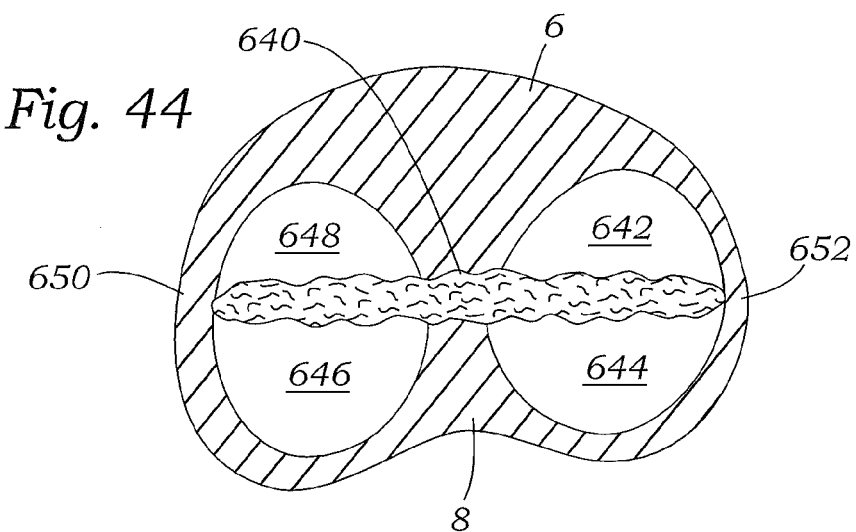
FIG. 44 shows an exemplary prosthetic device having an elongated body and two anchors, coupled to both of the native mitral valve leaflets, from an atrial view.
Figure 45:
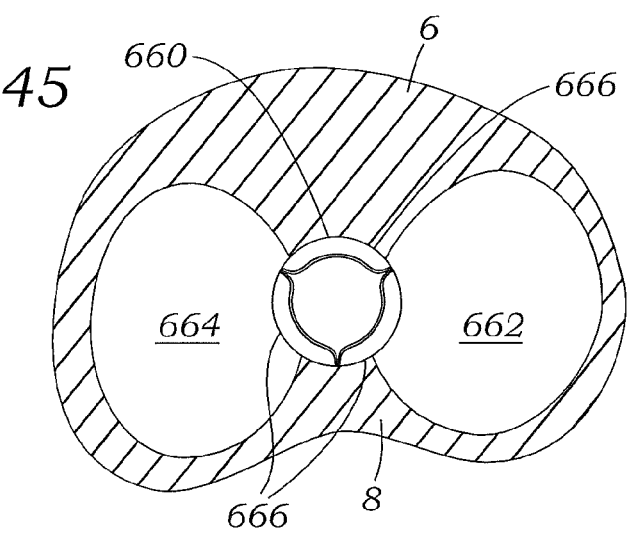
FIG. 45 shows an exemplary prosthetic device having a valve and two anchors, coupled to both of the native mitral valve leaflets, from an atrial view.

FIGS. 44 and 45 show alternative embodiments of dual anchor spacers clipped to the A2 and P2 regions of the anterior and posterior native leaflets 6, 8, as viewed from the left atrium. FIG. 44 shows an embodiment 640 in which the shape of the body of the spacer 640 is relatively elongate such that the spacer 640 extends substantially between the commissures 650, 652 of the mitral valve. As shown, in this embodiment, the native leaflets 6, 8 are brought toward one another by the anchors of the spacer 640, the overall area of the valve orifice is reduced, and the orifice is divided into four orifices 642, 644, 646, 648 during diastole. Thus, the area through which mitral regurgitation can occur is reduced, leaflet coaptation can be initiated at the location of the spacer 640, and the leaflets can fully coapt more easily, thereby preventing or minimizing mitral regurgitation. In addition, the shape of the spacer 640 can more effectively treat eccentric jet mitral regurgitation, because the extension of the body of the spacer 640 to the commissures 650, 652 helps the leaflets 6, 8, to coapt across the entirety of the native mitral valve orifice.

FIG. 45 shows an embodiment of a dual-anchor spacer 660 in which the body of the spacer 660 comprises a prosthetic valve having one or more flexible leaflets 666 that permit blood to flow into the left ventricle during diastole and block the back flow of blood into the left atrium during systole. In this embodiment, the native leaflets 6, 8 are brought closer to one another and the native mitral valve orifice is divided into two orifices 662, 664 during diastole. Because the body of the spacer 660 comprises a prosthetic valve, rather than a solid piece of material, the total effective open area between the leaflets during diastole (e.g., the area through which blood can flow) is greater in this embodiment than in the embodiment illustrated in FIGS. 43 and 44.

Figure 46:
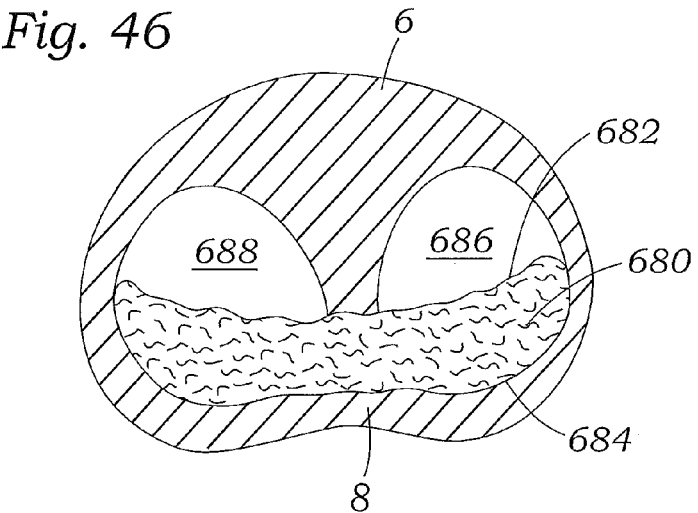
FIG. 46 shows an exemplary prosthetic device having a crescent-shaped body and two anchors, coupled to both of the native mitral valve leaflets, from an atrial view.

In alternative embodiments, the body of a dual anchor spacer can have various alternative shapes. For example, cross-sectional profile of the body can be circular, elliptical, or as shown in FIG. 46, can have a generally crescent shape. A spacer body having a crescent shape such as spacer body 680 in FIG. 46 (viewed from the left atrium) can be particularly advantageous because it can conform to the overall crescent shape of the anterior and posterior leaflets 6, 8 of the native mitral valve. In such an embodiment, the concave side 682 of the crescent shaped body 680 can face the anterior native leaflet 6 while the convex side 684 of the crescent shaped body 680 can face the posterior native leaflet 8. FIG. 46 shows that in such an embodiment, the native mitral valve orifice can be divided into two orifices 686, 688, each on the concave side 682 of the spacer 680, as the convex side 684 can conform to the posterior native leaflet 8 such that no openings exist between them.

Figure 47:
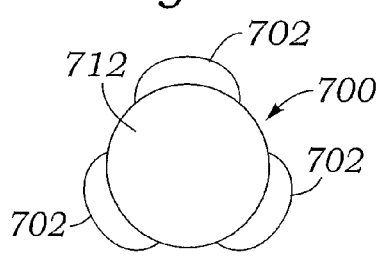
FIGS. 47-51 show exemplary prosthetic devices having three anchors.
Figure 48:
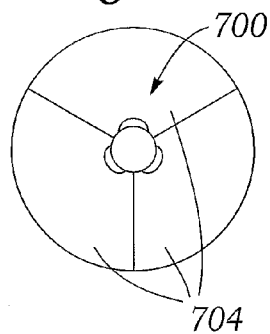
Figure 49:
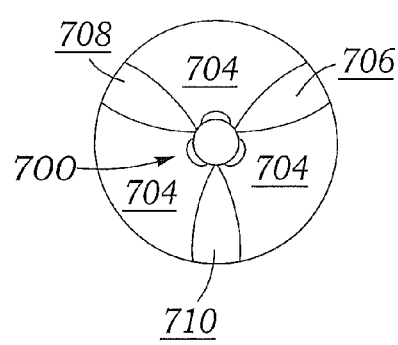
Figure 50:
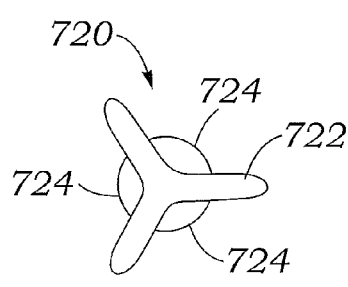
Figure 51:
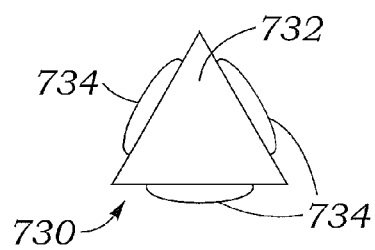

FIGS. 47-51 show embodiments of spacers having three anchors, which can be clipped to leaflets in the tricuspid valve of the human heart in a manner similar to that described above with regard to spacers in the mitral valve. FIG. 47 shows a tricuspid spacer 700 having a circular body 712 and three anchors 702. FIG. 48 shows the spacer 700 implanted in the tricuspid valve (as viewed from the right ventricle, as blood is being pumped out of the right ventricle), with each of the three anchors 702 clipped to a respective leaflet 704 of the tricuspid valve, and thereby coupling them to one another. FIG. 49 shows the spacer 700 clipped to the leaflets 704 of the tricuspid valve as blood is pumped from the right atrium to the right ventricle through orifices 706, 708, 710. FIG. 50 shows an alternative tricuspid spacer 720 having a body 722 and three clips 724. As shown, the body 722 can have a generally Y shape. FIG. 51 shows an alternative tricuspid spacer 730 having a body 732 and three clips 734. As shown, the body 732 can have a generally triangular shape.

Figure 52:
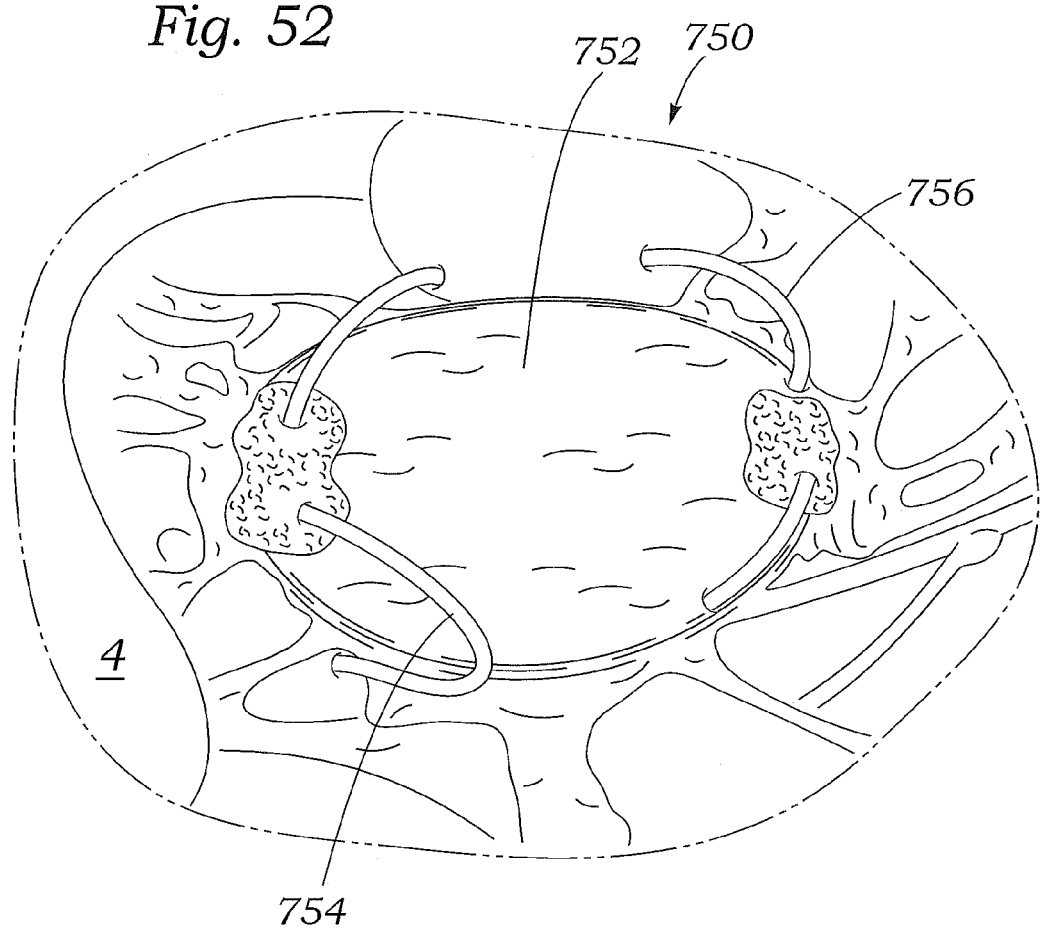
FIGS. 52-54 show the prosthetic device of FIGS. 38-41 implanted at a native mitral valve.
Figure 53:
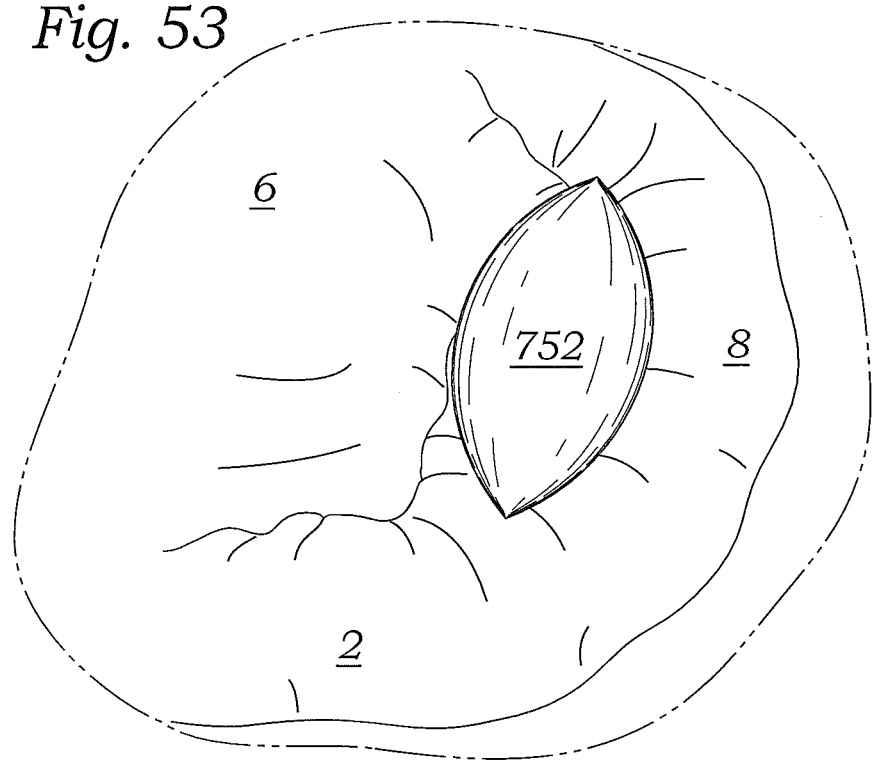
Figure 54:
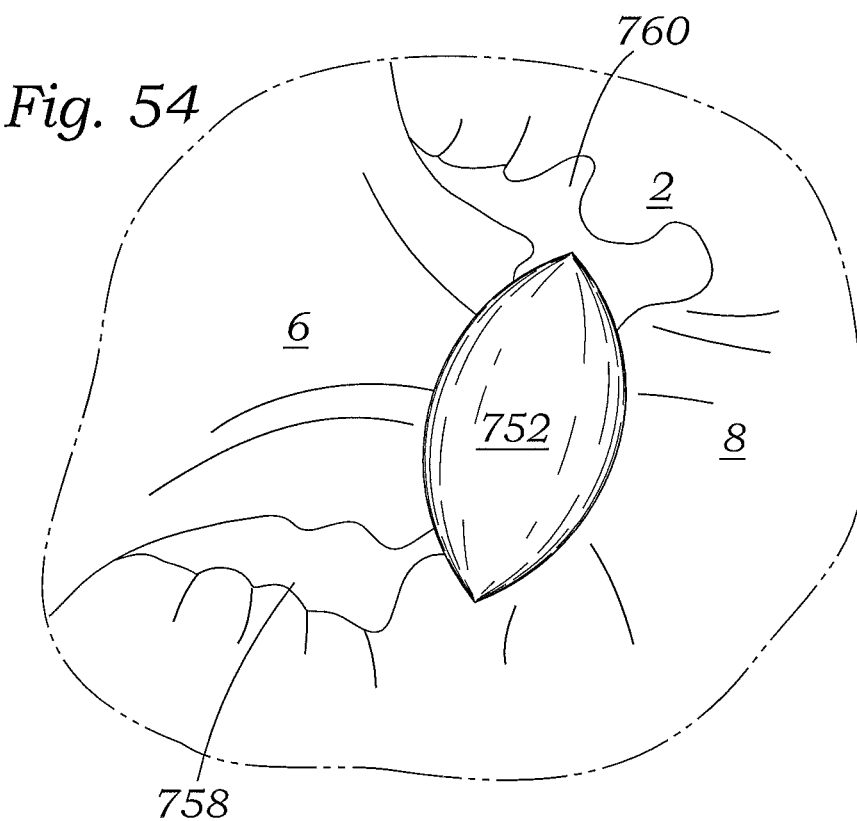

FIGS. 52-54 show an exemplary dual anchor spacer 750 having a body 752 and first and second anchors 754, 756, positioned within a native mitral valve. FIG. 52 shows the downstream end of the spacer 750 as seen from the left ventricle 4. FIG. 53 shows the upstream end of the spacer 750 as viewed from the left atrium 2 during systole, and FIG. 54 shows the upstream end of the spacer 750 from the left atrium 2 during diastole. As can be seen in FIG. 53, no openings appear through which regurgitant flow can occur. As can be seen in FIG. 54, two openings 758, 760 exist through which blood can flow from the left atrium 2 to the left ventricle 4 during diastole, as is desirable.

A suitable delivery sequence for delivering a prosthetic spacer such as spacer 750 to the mitral valve region of a patient's heart can comprise compressing a spacer to a compressed, delivery configuration, delivering the spacer to the coaptation line of a patient's native mitral valve, expanding the spacer until regurgitation in the patient's mitral valve is adequately reduced (an inflatable device can allow a physician to make fine adjustments to the final size and configuration of the spacer based on information received during the delivery process), manipulating the anchors of the spacer to an open position, capturing the native leaflets between the anchors and the body of the spacer, and then manipulating the anchors to a closed position, thereby clipping the spacer to the native mitral valve leaflets.

FIGS. 55 and 56 show an exemplary dual anchor spacer 800 comprising a main body 802 and first and second anchors 804, 806. The main body 802 can comprise a plurality of interconnected struts 808 which together form a plurality of open cells and are arranged to form a generally annular shape having first and second end portions 816, 818. The body 802 can be formed to be radially self-expandable. For example, the body 802 can be fabricated from a shape-memory material such as Nitinol, which can allow the spacer 800 to be radially compressed to a compressed delivery configuration, delivered to one of a patient's native heart valves, then self-expanded to an expanded functional configuration for use within the patient's heart.

The first anchor 804 can comprise first and second end portions 810, 812 which can be coupled to the first end portion 816 of the main body 802, and a loop portion 814 which can extend between the first and second end portions 810, 812. The first and second end portions 810, 812 can extend away from the first end portion 816 of the body 802, then curl back and extend toward the second end portion 818 of the main body 802. The loop portion 814 can be coupled to the first end portion 810, extend generally toward the second end portion 818 of the main body 802, curl back and extend toward the first end portion 816 of the main body 802, and be coupled to the second end portion 812.

Thus, the first anchor 804 can be coupled to the first end portion 816 of the main body 802 and extend along the side of the main body 802 toward its second end portion 818. The second anchor 806 can have a similar structure, and can be coupled to the main body 802 such that it extends along an opposing side of the main body 802. In this embodiment, the spacer 800 can be clipped to native tissues by pinching the native tissues between the anchors 804, 806 and the respective sides of the main body 802. The anchors 804, 806 can be made from various suitable materials, and in one exemplary embodiment can be fabricated from the shape-memory material Nitinol. The anchors 804, 806 in the illustrated embodiment are fabricated from separate pieces of material from the main body 802, and are coupled to the main body 802 using coupling mechanisms 820. The coupling mechanisms 820 can be, for example, crimping rings that extend around a strut at the first end 816 of the main body 802 and an adjacent portion of an anchor. In alternative embodiments, however, the anchors 804, 806 and the main body 802 can be fabricated integrally with one another (i.e., from a single piece of material). As best shown in FIG. 56, the main body 802 can have a generally elliptical or oval shape when viewed on end, but in alternative embodiments, the main body can be formed to have any of various suitable shapes when viewed on end, such as a circle.

FIGS. 57 and 58 show the spacer 800 covered in a blood impermeable fabric material 822, such as made of polyethylene terephthalate (PET) or polyurethane. The fabric material 822 can be relatively thick, strong, and soft, such as a knitted lofty cloth. The fabric material 822 can be selected to provide a softer surface for contact with the native tissue, thus reducing trauma caused to the native tissues by the implantation of the spacer 800, can be selected to promote native tissue ingrowth into the spacer 800, and/or can be selected to improve the seal formed between native tissues and the portions of the spacer 800 they come into contact with. Additionally, FIG. 58 shows that a fabric layer 824 can be disposed to cover all or substantially all of the opening at the center of the main body 802. The layer 824 can be blood impermeable, thereby blocking the flow of blood through the spacer 800. The layer 824 can be formed from the same material as fabric 822, and together the fabric 822 and layer 824 can work to prevent the regurgitant flow of blood through a heart valve when the spacer has been implanted therein.

FIGS. 59-63 illustrate exemplary systems and methods which can be used to implant the spacer 800 in a native heart valve. FIGS. 59-61 illustrate exemplary systems and steps which can be used to crimp the spacer 800 to a compressed, delivery configuration, suitable for delivery to a patient's native heart valve within a delivery device 850. FIG. 59 shows the spacer 800 with its main body 802 positioned in a crimper mechanism 900 capable of crimping the main body 802 to a compressed configuration. As shown, the anchors 804, 806 can remain outside the crimper mechanism 900 as it is used to crimp the main body portion 802. For example, U.S. Pat. No. 7,530,253, which is hereby incorporated herein by reference, describes an exemplary prosthetic valve crimping device that can be used to crimp the spacer 800.

In some embodiments, the delivery device 850 can be similar to the delivery device 2000 described in U.S. Patent Application Publication No. 2011/0137397 or the delivery devices described in U.S. Provisional Patent Application No. 61/760,577, and can be used to implant prosthetic devices via methods similar to those described therein. FIG. 59 shows that the delivery device 850 can include an inner sheath 852 provided with a pair of slots 854 disposed on opposing sides of the inner sheath 852, and an internal locking element 856, which is axially adjustable relative to the inner sheath 852 along a central longitudinal axis of the inner sheath 852. The internal locking element 856 can comprise a generally cruciform shape, having four extension portions 858 between which are defined four voids 860. As best shown in FIG. 59, two of the voids 860 can be aligned with the two slots 854, which can also be aligned with the portions of the anchors 804, 806 which are coupled to the body 802 of the spacer 800. Thus, in this embodiment, the locking element 856 can be retracted into the inner sheath 852, thereby pulling the main body portion 802 of the spacer 800 into the inner sheath 852 in the same direction. As best shown in FIG. 60, as the spacer 800 is pulled into the inner sheath 852, the first and second end portions 810, 812 of each of the anchors extend from the first end portion 816 of the spacer 800, through the respective voids 860 in the locking element, and then curl out of the slots 854 in the sides of the inner sheath 852, extending along the sides of the body 802 toward the second end portion 818 of the main body 802. In this way, the body 802 of the spacer 800 can be pulled into the inner sheath 852 and thereby compressed to a compressed delivery configuration.

As shown in FIG. 61, after the main body portion 802 has been situated within the inner sheath 852, an outer sheath 862 can be extended toward the distal end of the device 850 so as to enclose the anchors 804, 806, thereby causing them to wrap around the inner sheath 852 and be confined between the inner sheath 852 and outer sheath 862.

Figure 62:
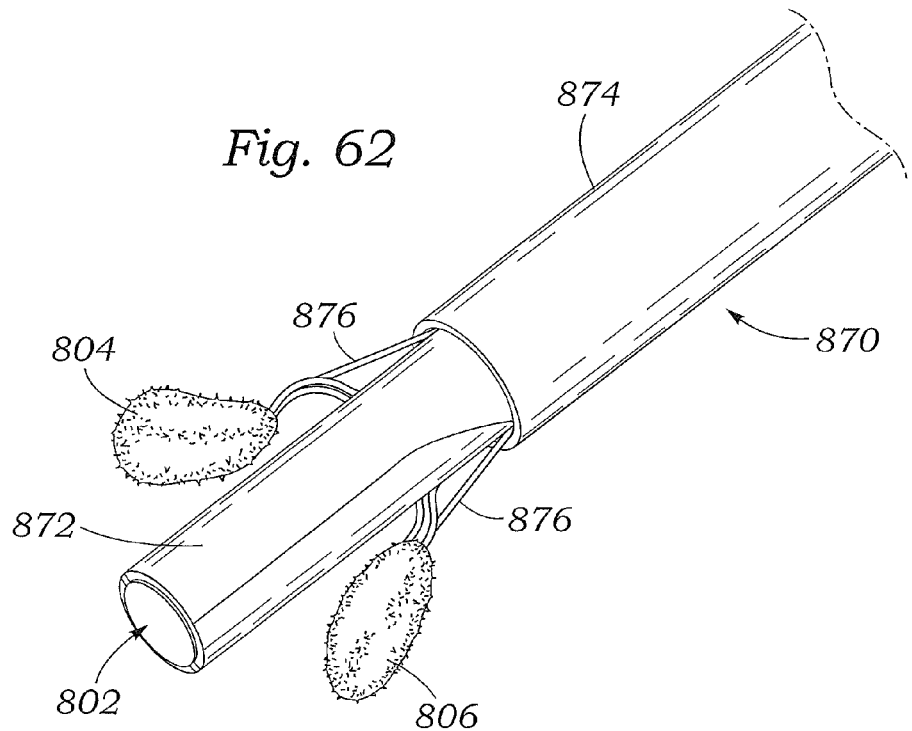
Figure 63:
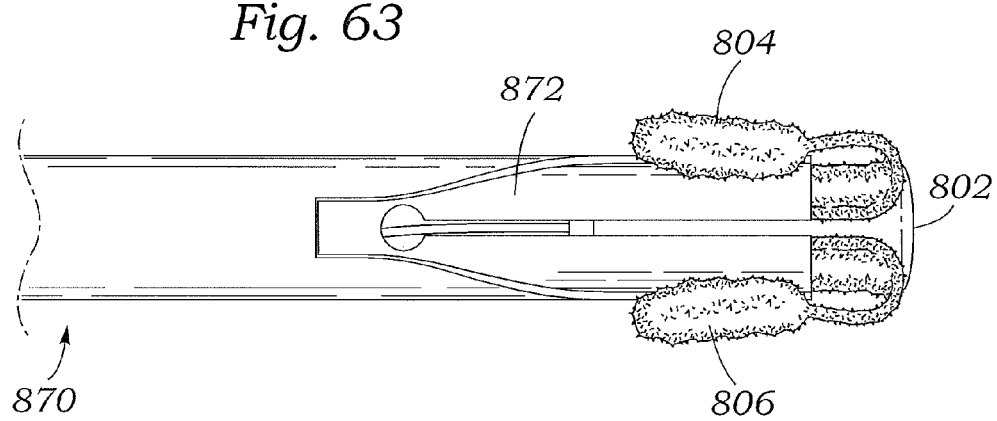

FIGS. 62 and 63 show a spacer 800 covered in fabric as described above and situated within a delivery device 870 in two different configurations. FIG. 62 shows the spacer 800 having its main body portion 802 situated within an inner sheath 872 of the delivery device 870 such that the anchors 804, 806 extend toward a distal end portion of the delivery device 870. In this embodiment, an outer sheath 874 can be extended distally to retain and secure the anchors 804, 806 against the sides of the inner sheath 872. Such a configuration can be used to deliver the spacer transapically, as described below. In some embodiments, retraction of the outer sheath 874 can allow the anchors 804, 806 to self-expand to a splayed-apart configuration.

FIG. 62 also shows that forcible expanders, or levers, 876 can be used to force the anchors 804, 806 to splay apart. The forcible expanders 876 can be radially self-expanding levers which radially self-expand when the outer sheath 874 is retracted or are otherwise configured to radially expand away from the inner sheath when they are actuated by a physician (such as by actuating a control knob on a handle that is operatively connected to the expanders 876). The expanders 876 can alternatively be sutures or other mechanisms which can be actuated by a physician to force the anchors 804, 806 to splay apart. In some embodiments, retraction of the outer sheath 874 can allow the anchors 804, 806 to self-expand to a first splayed-apart configuration, and forcible expanders 876 can be actuated to force the anchors 804, 806 to further radially expand to a second splayed-apart configuration. In such an embodiment, the expanders 876 can be actuated to cause the anchors 804, 806 to radially expand to the second splayed apart configuration, and can then be actuated to allow the anchors 804, 806 to move radially inward and return to the first splayed-apart configuration.

FIGS. 62 and 63 illustrate the spacer 800 situated within the delivery system 870 such that the anchors 804, 806 extend generally along the outside of the body 802 toward the second end portion 818 of the spacer 800. In alternative embodiments, however, the configuration of the body 802 and anchors 804, 806 within the delivery system 870, and the deployment of the spacer 800 from the delivery system 870, can be similar to that illustrated in FIGS. 12-15 with respect to device 50 and delivery catheter 56.

FIG. 63 shows the spacer 800 having its main body portion 802 situated within the inner sheath 872 of the delivery device 870 such that the anchors 804, 806 extend toward a proximal end portion of the delivery device 870. In this embodiment, the outer sheath 874 can be extended distally to retain and secure the anchors 804, 806 against the sides of the inner sheath 872. Such a configuration can be used to deliver the spacer transatrially, as described below.

Prosthetic spacers described herein can be delivered using minimally invasive approaches. FIGS. 64-67 show various approaches by which a prosthetic spacer 800 can be delivered to the region of a patient's mitral valve using a delivery system 920. For example, a prosthetic spacer can be delivered via a transapical approach (FIG. 64), via a transseptal approach (FIG. 65), via a transatrial approach (FIG. 66), or via a transfemoral approach (FIG. 67). FIGS. 64-67 show that the delivery system 920 can comprise an outer sheath 922, an inner sheath 924, and a guidewire 930 which can extend through the outer sheath 922 and inner sheath 924. The delivery system 920 can also include a pusher element (not illustrated in FIGS. 64-67, but similar to those described above), which can be actuated to move the spacer 800 within the inner sheath 924. The outer sheath 922, inner sheath 924, guidewire 930, and pusher element can each be retracted proximally or extended distally with respect to one another. The guidewire 930 can be used to guide the delivery of the other components of the system 920 to an appropriate location within a patient's vasculature. The guidewire 930 can extend through a small opening or pore in the spacer 800, for example in the fabric layer 824, the small opening or pore being small enough that substantial blood cannot flow therethrough.

Figure 64:
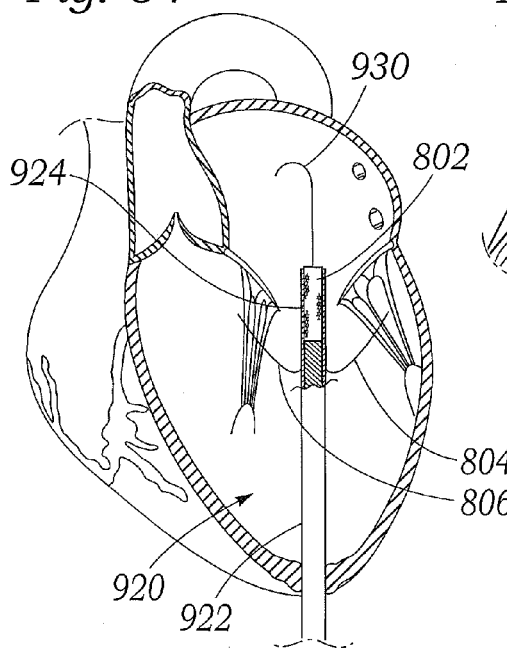
FIGS. 64-67 show various exemplary delivery approaches for delivering a prosthetic device to a native mitral valve.

FIGS. 64 and 67 show that the deployment of the spacer 800 to a native mitral valve via the transapical approach can be similar to the deployment of the valve 800 via the transfemoral approach, at least because in both cases the valve is delivered to the mitral valve from the left ventricle. In preparing the delivery system 920 for delivery of the spacer 800 via the transapical or the transfemoral approach, the spacer 800 can be situated within the system 920 with the second end portion 818 of the spacer 800 disposed at the distal end of the system 920 (such as shown in FIG. 62). In the transapical and the transfemoral approaches, the delivery system 920 can be used to first deliver the spacer 800 to the region of the native mitral valve from the left ventricle. In the transapical approach, the delivery device 920 is inserted into the left ventricle via an opening in the chest and the apex of the heart. In the transfemoral approach, the delivery device 920 can be inserted into a femoral artery and advanced through the aorta in a retrograde direction until the distal end of the delivery device is in the left ventricle. The outer sheath 922 can be retracted proximally such that the anchors 804, 806 are no longer confined within the outer sheath 922. In some embodiments, the anchors 804, 806 can be configured to self-expand to a splayed apart configuration shown in FIGS. 64 and 67. In other embodiments, as described above, the delivery system 920 can include a mechanism for forcing the anchors 804, 806 to splay apart to the splayed-apart configuration (such as described above with respect to the embodiment of FIG. 62).

The device 920 can then be distally advanced so that the native mitral valve leaflets are positioned between the splayed apart anchors 804, 806, and the body 802. The inner sheath 924 can then be retracted so that the body 802 is no longer confined within the inner sheath 924 and can radially expand to an expanded configuration between the native mitral valve leaflets. In some embodiments, the body 802 can expand such that the native leaflets are pinched between the body 802 and the anchors 804, 806. In alternative embodiments, as described above, the mechanism for forcing the anchors 804, 806 to splay apart can be actuated to allow the anchors 804, 806 to move radially inward toward the main body 802, thereby pinching the native leaflets between the main body 802 and the anchors 804, 806.

Figure 65:
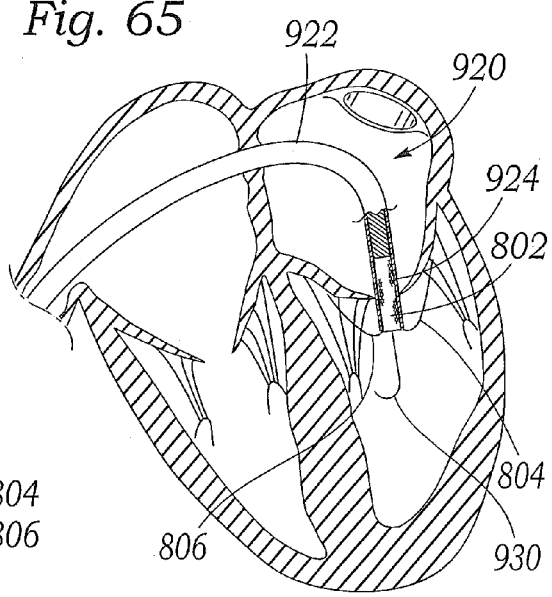
Figure 66:
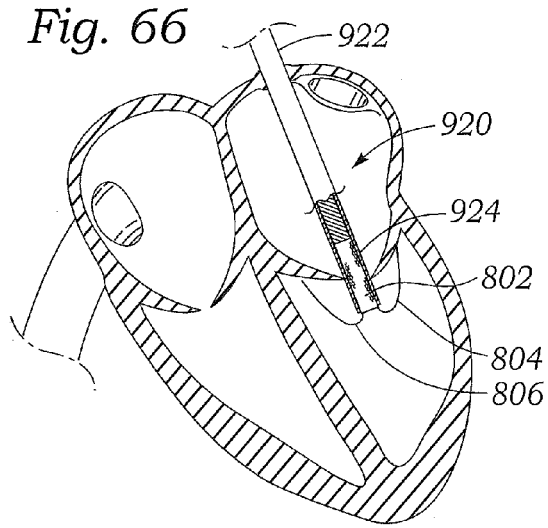
Figure 67:
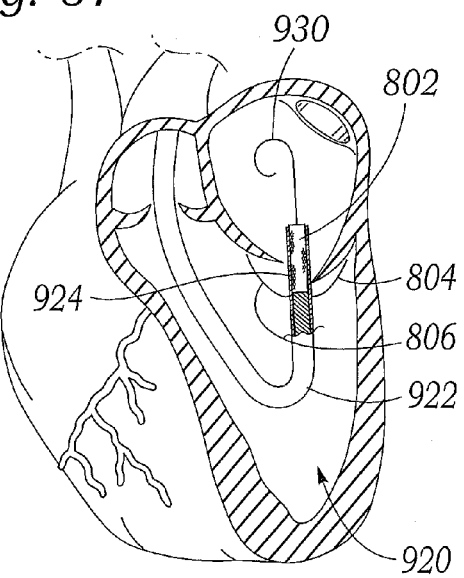

FIGS. 65 and 66 show that the deployment of the spacer 800 to a native mitral valve via the transseptal approach can be similar to the deployment of the valve 800 via the transatrial approach, at least because in both cases the valve is delivered to the mitral valve from the left atrium. In preparing the delivery system 920 for delivery of the spacer 800 via the transseptal or the transatrial approach, the spacer 800 can be situated within the system 920 with the first end portion 816 of the spacer 800 disposed at the distal end of the system 920 (such as shown in FIG. 63). In these approaches, the delivery system 920 can be used to first deliver the spacer 800 to the region of the native mitral valve from the left atrium. The outer sheath 922 can then be retracted proximally such that the anchors 804, 806 are no longer confined within the outer sheath 922. In some embodiments, the anchors 804, 806 can be configured to self-expand to a splayed apart configuration shown in FIGS. 65 and 66. In other embodiments, as described above, the delivery system 920 can include a mechanism for forcing the anchors 804, 806 to splay apart to the splayed-apart configuration.

The system 920 can then be proximally retracted so that the native mitral valve leaflets are positioned between the splayed apart anchors 804, 806, and the body 802. The inner sheath 924 can then be retracted so that the body 802 is no longer confined within the inner sheath 924 and can radially expand to an expanded configuration between the native mitral valve leaflets. In some embodiments, the body 802 can expand such that the native leaflets are pinched between the body 802 and the anchors 804, 806. In alternative embodiments, as described above, the mechanism for forcing the anchors 804, 806 to splay apart can be actuated to allow the anchors 804, 806 to move radially inward toward the main body 802, thereby pinching the native leaflets between the main body 802 and the anchors 804, 806.

In any of the four approaches described above, once the native leaflets have been captured by the spacer 800, the delivery system 920 can be retracted and removed from the patient's vasculature. The spacer 800 can remain in the native mitral valve region, with the main body 802 being situated between the two native leaflets, thereby helping to reduce or prevent mitral regurgitation. It will be understood that similar techniques can be used to deliver a spacer to the native aortic, tricuspid, or pulmonary valves, depending on the needs of the patient.

In any of the four approaches described above, a marker catheter or other similar device can be used to help coordinate delivery and ensure that a desirable delivery position is achieved. An exemplary suitable marker catheter can include a standard catheter designed for angiograms, for example, a catheter made of a relatively low-density plastic material having relatively high-density metal marker bands (e.g., radiopaque marker bands) disposed at regular intervals thereon. Thus, the device can be introduced into a patient's vasculature and can be viewed under echocardiography or fluoroscopy. Alternatively, a marker wire can be used in place of the marker catheter. Another suitable alternative technique is left atrium angiography, which can help a physician visualize components of a patient's heart.

A marker catheter or marker wire can be introduced into a patient's vasculature and advanced to specific areas of the vasculature near a patient's heart. For example, a marker catheter can be advanced from a patient's jugular or femoral vein into the right atrium, then into the patient's coronary sinus. As another example, a marker catheter can be advanced from a patient's femoral artery to the patient's circumflex artery. As another example, a marker catheter can be advanced into a patient's left atrium. Once situated in the coronary sinus, circumflex artery, left atrium, or other suitable area of a patient's vasculature, the marker catheter can be used to aid a physician in delivering and ensuring desirable implantation of a prosthetic device. For example, the coronary sinus extends around the heart near the location and elevation of the mitral valve and thus can help a physician to properly size and position a prosthetic device for implantation.

For example, the patient's vasculature can be viewed under echocardiography, fluoroscopy, or other visualization technique which allows a physician to view the prosthetic device being delivered and the marker catheter. A physician can first view the devices along an axis extending from the patient's left atrium to the patient's left ventricle (referred to as a "short axis"). By viewing the devices along the short axis, a physician can deploy (such as by inflating a balloon on which an implantable device is mounted) an implantable prosthetic device and expand portions of the device to desired sizes and/or configurations based on the size and location of the marker catheter, which can provide an estimate of the size of features of the native mitral valve. Alternatively or additionally, a physician can use the marker catheter to obtain an estimate of the size of a patient's native heart valve, from which estimate a prosthetic device to be implanted in the patient's native heart valve can be selected from a set of devices having differing sizes, e.g., a set of devices having differing diameters.

A physician can also view the devices along an axis perpendicular to the short axis (referred to as a "long axis"). The long axis can have several orientations, such as from commissure to commissure, but in one specific embodiment, the long axis is oriented from the A2 location to the P2 location of the native mitral valve. By viewing the devices along the long axis, a physician can align an implantable prosthetic device relative to the marker catheter at a desirable location along the short axis, such that an atrial anchor of the implantable device is situated in the left atrium (above the marker catheter) and a ventricular anchor of the implantable device is situated in the left ventricle (below the marker catheter).

Figure 68:
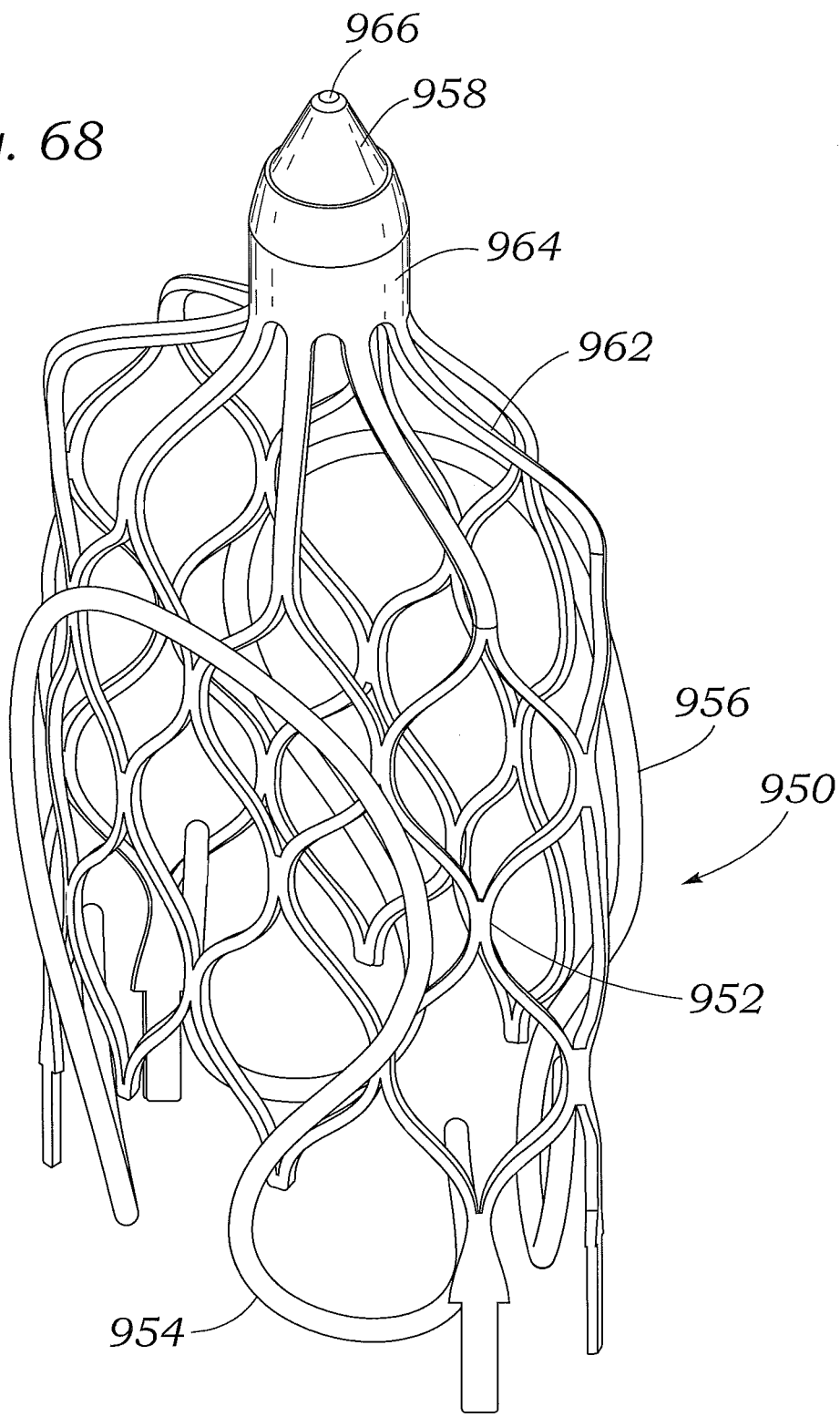
FIG. 68 shows an exemplary prosthetic device including a nosecone.

FIG. 68 shows an exemplary dual anchor spacer 950 which can be delivered to the region of the native mitral valve via any suitable delivery method, for example, using the transapical, transeptal, transatrial, or transfemoral techniques described above. The spacer 950 can include a main body 952, a first anchor 954, a second anchor 956, and a nosecone 958. The spacer 950 can also include a tapered portion 962, which can couple the main body portion 952 to a neck portion 964. The taperer portion 962 can have a variable width which can taper from the width of the main body 952 to the width of the neck portion 964. The neck portion 964 can be configured to receive a portion of the nosecone 958 therein, and can be coupled to the nosecone 958. The main body 952 and anchors 954, 956 can be fabricated from various materials, as described above with regard to other embodiments, and the nosecone 958 can be fabricated from various suitable materials such as a long term implantable silicone or other suitable elastomers.

The nosecone 958 can have a small pore, or opening, or slit, 966, which can extend through and along the length of the nosecone 958. In accordance with suitable delivery methods making use of a guidewire such as guidewire 930, the guidewire can extend through the opening 966, thus eliminating the need for an opening or pore in a fabric layer. The spacer 950 can facilitate crossing of a native heart valve due to its tapered tip, which can also provide improvements in hydrodynamics during diastolic blood flow. When a guidewire is removed from the opening 966, the opening can close under its own resiliency and/or blood pressure, thus leaving a sealed spacer implanted at a native heart valve. Alternatively, or in addition, the opening 966 can be sufficiently small to prevent significant amounts of blood from travelling through the nosecone 958.

The multi-anchor spacers described herein offer several advantages over previous techniques for treating regurgitation in heart valves. For example, the multi-anchor spacers described herein can be used to treat patients whose native leaflets fail to coapt at all, whereas many previous techniques required some amount of native coaptation to be efficacious. Additionally, the spacers described herein (e.g., spacer 640) can treat eccentric jet regurgitation more readily than other known techniques. While embodiments have been illustrated with two and three anchors, the techniques described herein are generally application to spacers having any number of anchors.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles disclosed herein may be applied, it should be recognized that the illustrated embodiments are only preferred examples and should not be taken as limiting the scope of the disclosure. Rather, the scope is defined by the following claims. We therefore claim all that comes within the scope and spirit of these claims.

We claim:

1. A method of implanting a prosthetic sealing device at a native mitral valve of a heart, the method comprising:
   advancing a delivery system to a native mitral valve region of a heart, the delivery system housing the prosthetic sealing device in a radially compressed configuration, the prosthetic sealing device comprising a main body and anchors extending from the main body, the main body comprising a radially expandable and compressible annular metal frame having an upstream end, a downstream end, and a lumen extending from the upstream end to the downstream end, the main body further comprising a blood impermeable fabric covering the frame;
   proximally retracting an outer sheath of the delivery system such that the anchors of the prosthetic sealing device are not confined within the delivery system;
   positioning the delivery system such that native mitral valve leaflets are positioned between the anchors of the prosthetic sealing device and the delivery system;
   proximally retracting an inner sheath of the delivery system such that the main body of the prosthetic sealing device is not confined within the delivery system and expands from the radially compressed configuration to a radially expanded configuration and is held between the native mitral valve leaflets by the anchors, which clamp portions of the native leaflets against the main body, wherein the fabric prevents blood from flowing through the lumen of the metal frame during systole and during diastole, wherein non-clamped portions of the native mitral valve leaflets can move away from the main body of the prosthetic device during diastole to allow blood from the left atrium to flow past the prosthetic device into the left ventricle, and the non-clamped portions of the native mitral valve leaflets can seal against the main body of the prosthetic device during systole to minimize mitral regurgitation; and removing the delivery system from the native mitral valve region of the heart;

wherein an upstream end of the prosthetic sealing device is located downstream of the native mitral valve annulus when implanted.

2. The method of claim 1, wherein advancing the delivery system to the native mitral valve region comprises inserting the delivery device into a left ventricle through an incision in an apex of the left ventricle.

3. The method of claim 1, wherein when the delivery system is advanced to the native mitral valve region of the heart, the anchors are held in a substantially straightened position within the delivery catheter extending distally along a side of the body of the prosthetic sealing device.

4. The method of claim 1, wherein the main body comprises an upstream end portion and a downstream end portion, wherein the upstream end portion is tapered.

5. The method of claim 4, wherein the tapered upstream end portion supports a tapered polymeric nose cone defining a guide wire lumen.

6. The method of claim 1, wherein the upstream end of the metal frame defines an opening and the fabric blocks blood in the left atrium from flowing into the lumen of the frame during diastole.

7. The method of claim 1, further comprising, after retracting the outer sheath, applying an expansion force to the anchors to cause the anchors to splay apart from the main body so that the anchors can be placed behind the native leaflets.

8. The method of claim 7, further comprising, after the main body is expanded, removing the expansion force to allow the anchors to pivot radially inwardly under their own resiliency to clamp the leaflets against the main body.

9. The method of claim 7, wherein the expansion force is applied by expanders that are actuated by a user to cause the anchors to splay apart.

10. The method of claim 9, wherein the expanders are levers.

11. The method of claim 1, wherein advancing the delivery system to the native mitral valve region comprises advancing the delivery system via a trans-septal delivery approach in which the delivery system is advanced through an opening made in a septum between the a left atrium and a right atrium of the heart.

12. The method of claim 1, wherein the fabric comprises a knitted lofty cloth.

13. The method of claim 1, wherein the metal frame comprises a plurality of interconnected struts defining a plurality of openings that are covered by the fabric covering.

14. A method of implanting a prosthetic sealing device at a native mitral valve of a heart, the method comprising:

advancing a delivery system to a native mitral valve region of a heart, the delivery system housing the prosthetic sealing device in a radially compressed configuration, the prosthetic sealing device comprising a main body and anchors extending from the main body, the main body having an upstream end and a downstream end;

proximally retracting an outer sheath of the delivery system such that the anchors of the prosthetic sealing device are not confined within the delivery system;

applying an expansion force to the anchors to cause the anchors to splay apart from the main body so that the anchors can be placed behind the native leaflets;

positioning the delivery system such that native mitral valve leaflets are positioned between the anchors of the prosthetic sealing device and the delivery system;

proximally retracting an inner sheath of the delivery system such that ft the main body of the prosthetic sealing device is not confined within the delivery system and expands from a radially compressed configuration to a radially expanded configuration;

removing the expansion force to allow the anchors to pivot radially inwardly under their own resiliency to clamp the leaflets against the main body, thereby anchoring the main body between the native mitral valve leaflets, wherein the main body is impermeable to blood so as to prevent blood from flowing through the main body from the upstream end to the downstream end during systole and during diastole; and removing the delivery system from the native mitral valve region of the heart.

15. The method of claim 14, wherein advancing the delivery system to the native mitral valve region comprises advancing the delivery system into a right atrium of the heart, through an incision in a portion of a septum between a left atrium and the right atrium, and into the left atrium.

16. The method of claim 14, wherein when the delivery system is advanced to the native mitral valve region of the heart, the anchors are held in a substantially straightened position within the delivery catheter extending proximally from body of the prosthetic sealing device.

17. The method of claim 14, wherein the main body comprises an upstream end portion and a downstream end portion, wherein the upstream end portion is tapered.

18. The method of claim 14, wherein the main body comprises a radially expandable and compressible annular metal frame defining the upstream end and the downstream end of the main body, the frame having a lumen extending from the upstream end to the downstream end, the main body further comprising a blood impermeable fabric covering the frame that prevents blood from flowing through the lumen during systole and diastole.

19. The method of claim 18, wherein the fabric comprises a knitted lofty cloth.

20. The method of claim 14, wherein the expansion force is applied by expanders that are actuated by a user to cause the anchors to splay apart.

21. The method of claim 20, wherein the expanders are levers.

22. The method of claim 14, wherein advancing the delivery system to the native mitral valve region comprises inserting the delivery device into a left ventricle of the heart through an incision in an apex of the left ventricle.

23. The method of claim 14, wherein an upstream end of the prosthetic sealing device is located below the native mitral valve annulus when implanted.

* * * * *

UNITED STATES PATENT AND TRADEMARK OFFICE
CERTIFICATE OF CORRECTION

PATENT NO. : 9,510,946 B2
APPLICATION NO. : 14/011598
DATED : December 6, 2016
INVENTOR(S) : Chau et al.

Page 1 of 1

It is certified that error appears in the above-identified patent and that said Letters Patent is hereby corrected as shown below:

In the Specification

Column 3, Line 53, delete "ammlus" and insert -- annulus --.

Column 9, Line 33, delete "tendinae" and insert -- tendineae --.

In the Claims

Column 30, Line 17, in Claim 14, delete "that ft the" and insert -- that the --.

Signed and Sealed this
Thirtieth Day of January, 2018

Joseph Matal
*Performing the Functions and Duties of the
Under Secretary of Commerce for Intellectual Property and
Director of the United States Patent and Trademark Office*